United States Patent [19]

Kitaura et al.

[11] Patent Number: 4,476,050
[45] Date of Patent: * Oct. 9, 1984

[54] PEPTIDE, PROCESS FOR PREPARATION THEREOF AND USE THEREOF

[75] Inventors: Yoshihiko Kitaura, Sakurai; Osamu Nakaguchi, Toyonaka; Keiji Hemmi, Suita; Satoshi Yonishi, Kadoma; Hidekazu Takeno, Tenri; Satoshi Okada, Takatsuki; Masashi Hashimoto, Takarazuka, all of Japan

[73] Assignee: Fujisawa Pharmaceutical Co., Ltd., Osaka, Japan

[*] Notice: The portion of the term of this patent subsequent to Jul. 17, 2001 has been disclaimed.

[21] Appl. No.: 341,057

[22] Filed: Jan. 20, 1982

[30] Foreign Application Priority Data

Jan. 29, 1981 [GB] United Kingdom ................. 8102709

[51] Int. Cl.³ ........................................... C07C 103/52
[52] U.S. Cl. ........................................... 260/112.5 R
[58] Field of Search ................... 260/112.5 R; 424/177

[56] References Cited

U.S. PATENT DOCUMENTS 4,261,979  4/1981  Jolles et al. ................. 260/112.5 R
4,311,640  1/1982  Kuroda et al. ............... 260/112.5 R

OTHER PUBLICATIONS

Ariën, *Drug Design*, vol. II, N.Y. Academic Press, 1971, p. 338-341, 355, 360-362.

Kitaura et al., "European Patent Application", Ser. No. 11,283, 5-20-80.
Dezelee et al., "Biochemistry", vol. 9, No. 4, 1970, pp. 823-831.

*Primary Examiner*—Delbert R. Phillips
*Assistant Examiner*—F. T. Moezie
*Attorney, Agent, or Firm*—Oblon, Fisher, Spivak, McClelland & Maier

[57] ABSTRACT

The invention deals with novel peptides useful in the therapeutic treatment of infectious diseases caused by pathogenic microorganisms having the structure:

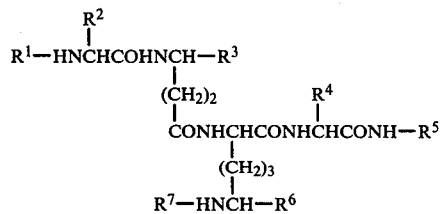

wherein,
$R^1$ is hydrogen or acyl,
$R^2$ is lower alkyl,
$R^3$ is carboxy or protected carboxy,
$R^4$ is hydrogen or lower alkyl,
$R^5$ is hydrogen, alkyl or ar(lower)alkyl,
$R^6$ is carboxy or protected carboxy, and
$R^7$ is hydrogen or an amino protective group,
and their pharmaceutically acceptable salts.

6 Claims, No Drawings

PEPTIDE, PROCESS FOR PREPARATION THEREOF AND USE THEREOF

This invention relates to a new peptide. More particularly, this invention relates to a new peptide and the pharmaceutically acceptable salt thereof, which have pharmacological activities, to processes for the preparation thereof and to a new intermediate for preparing the active peptide, and to the pharmaceutical composition comprising the same and a method of use thereof.

A new peptide of this invention is represented by the following formula (I):

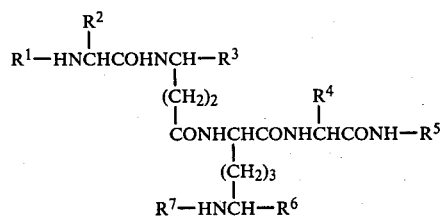

wherein
$R^1$ is hydrogen or acyl,
$R^2$ is lower alkyl,
$R^3$ is carboxy or protected carboxy,
$R^4$ is hydrogen or lower alkyl,
$R^5$ is hydrogen, alkyl or ar(lower)alkyl,
$R^6$ is carboxy or protected carboxy, and
$R^7$ is hydrogen or an amino protective group.

Particulars of the various definitions, which are mentioned hereinabove and hereinafter, and preferred examples thereof are explained in the following.

The term "lower" is intended to mean a group having 1 to 8 carbon atoms, unless otherwise provided.

(1) Re. Acyl for $R^1$ and $R_a^1$:

As suitable examples of acyl, there may be exemplified alkanoyl, alkoxycarbonyl, aralkanoyl or the like.

As suitable example of alkanoyl, there may be exemplified acetyl, propionyl, butyryl, isobutyryl, valeryl, isovaleryl, pivaloyl, hexanoyl, α-ethylhexanoyl, heptanoyl, octanoyl, lauroyl, stearoyl, n-docosanoyl and the like.

As suitable examples of alkoxycarbonyl, there may be exemplified lower alkoxycarbonyl such as methoxycarbonyl, ethoxycarbonyl, propoxycarbonyl, butoxycarbonyl, t-butoxycarbonyl, t-pentoxycarbonyl or the like.

In the above exemplified alkanoyls and alkoxycarbonyl, the aliphatic hydrocarbon moiety may have optionally one or more suitable substituent(s) such as halogen (e.g. fluorine, chlorine, bromine, etc.), hydroxy, carboxy and the like.

As suitable example of alkanoyls having such substituent, there may be exemplified hydroxy(lower)alkanoyl such as 2-hydroxypropionyl (i.e. lactoyl).

As suitable example of aralkanoyl, there may be exemplified ar(lower)alkanoyl such as phenyl(lower)alkanoyl (e.g. phenylacetyl, etc.) or the like.

In the above exemplified aralkanoyl, the aromatic hydrocarbon moiety and/or the aliphatic hydrocarbon moiety may have optionally one or more suitable substituent(s), such as the same as those exemplified as the suitable substituent for the alkanoyl.

Among said substituted aralkanoyl, as suitable examples there may be exemplified phenyl(lower)hydroxyalkanoyl such as mandelyl and the like.

In the above exmplified acyl, in case that said acyl has one or more functional group(s) such as hydroxy, amino and carboxy, such a functional group may be protected by a conventional protective group to form protected hydroxy, protected amino and protected carboxy.

(2) Re. Lower alkyl for $R^2$:

Suitable example of lower alkyl is one having 1 to 6 carbon atoms such as methyl, ethyl, propyl, isopropyl, butyl, isobutyl, pentyl, isopentyl and the like.

(3) Re. Protected carboxy for $R^3$, $R_a^3$, $R^6$, $R_a^6$ and functional group in the acyl for $R^1$:

A protective group of the protected carboxy includes a conventional carboxy protective group which is conventionally used in the field of amino acid and peptide chemistry.

As suitable examples of protected carboxy, there may be exemplified an ester such as an ester with silyl compound, an ester with an aliphatic hydroxy compound and an ester with a hydroxy compound containing an aromatic group, and a protected carbazoyl of the formula: —CONHNHY (wherein Y is hydrogen or an amino protective group).

As more suitable examples of protected carboxy, there may be exemplified alkyl such as lower alkyl (e.g. methyl, ethyl, etc.) ester, aralkyl such as mono- or di-phenyl(lower)alkyl (e.g. benzyl, diphenylmethyl, etc.) ester and the like.

(4) Re. Alkyl for $R^5$:

As suitable examples of alkyl, there may be exemplified one having 1 to 20 carbon atoms such as methyl, ethyl, propyl, isopropyl, butyl, pentyl, hexyl, heptyl, octyl, dodecyl, (lauryl), octadecyl (stearyl) or the like.

(5) Re. Ar(lower)alkyl for $R^5$:

As suitable examples of ar(lower)alkyl, there may be exemplified phenyl ($C_1$ to $C_5$) alkyl such as benzyl, phenetyl, phenylpropyl or the like.

(6) Re. Amino protective group for $R^7$, $R_a^7$, $R_b^7$ and Y, and the functional group in the acyl group for $R^1$ and $R_a^1$:

The amino protective group includes a conventional amino protective group which is used in the field of amino acid and peptide chemistry.

As suitable examples of the amino protective group, there may be exemplified alkoxycarbonyl such as lower alkoxycarbonyl (e.g. methoxycarbonyl, ethoxycarbonyl, propoxycarbonyl, butoxycarbonyl, t-butoxycarbonyl, t-pentoxycarbonyl, etc.), aralkoxycarbonyl such as phenyl(lower)alkoxycarbonyl (e.g. benzyloxycarbonyl, etc.) and the like.

(7) Re. Hydroxy protective group in the acyl for $R^1$:

As suitable example of a hydroxy protective group in the acyl group for $R^1$ and $R_a^1$, there may be exemplified a conventional one, for example, acyl such as alkanoyl (e.g. acetyl, etc.).

A pharmaceutically acceptable salt of the new peptides of the formula (I) may include a salt with an inorganic or organic base such as an alkali metal salt (e.g. sodium salt, potassium salt, etc.), an alkaline earth metal salt (e.g. calcium salt, etc.), ammonium salt, organic amine salt (e.g. ethanolamine salt, triethylamine salt, dicyclohexylamine salt, etc.) or the like, and an acid addition salt with organic or inorganic acid such as methane sulfonate, trifluoroacetate, hydrochloride, sulfate, nitrate, phosphate or the like.

The compound (I) of this invention can be prepared by various methods, details of which will be apparent from the following descriptions.

(1) Process 1: Peptide bond formation

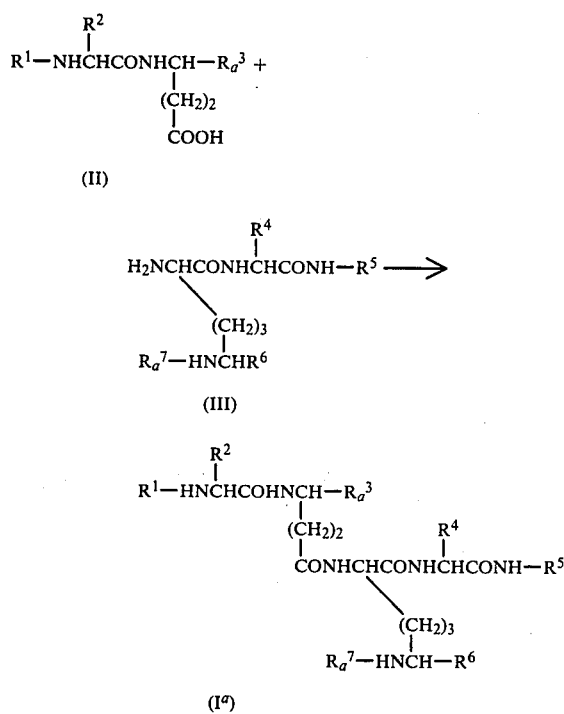

(II)

(III)

(Iᵃ)

(2) Process 2: Elimination of protective groups:

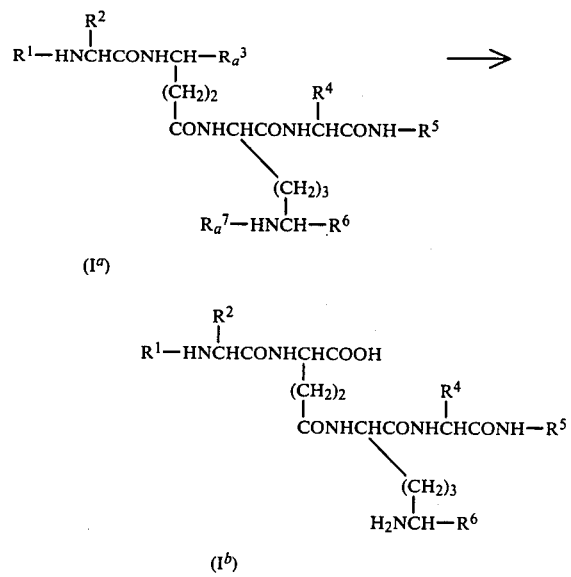

(Iᵃ)

(Iᵇ)

(3) Process 3: Deacylation:

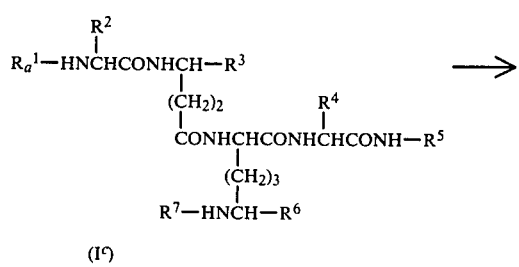

(Iᶜ)

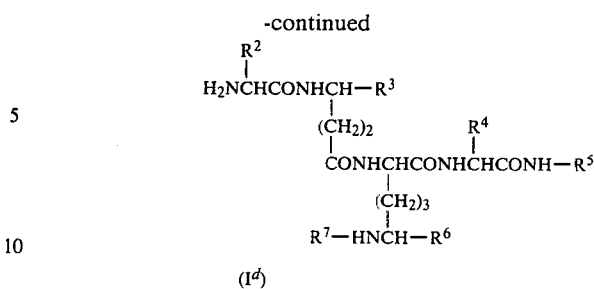

(Iᵈ)

In the above formulae, $R_a^1$ is acyl, $R_a^3$ is protected carboxy, $R_a^7$ is an amino protective group, and $R^1$, $R^2$, $R^3$, $R^4$, $R^5$ and $R^6$ are each as defined above.

Detailed explanation of processes for preparing of the compound (I) will be made in the following:

(1) Process 1: Peptide bond formation Compound (II)+Compound (III)→Compound (Ia)

This process relates to a method for preparing Compound (Ia) by reacting Compound (II) or its salt with a Compound (III) or its salt.

The reaction of this process can be conducted as follows.

That is, in one case, as the first step, the carboxy group of Compound (II) or its salt is usually activated in a conventional manner, for example, in the form of its acid halide, acid anhydride or a mixed anhydride, activated ester, and the like, and is reacted with the Compound (III) to give Compound (Ia), and in the other case, the Compound (II) or its salt is reacted with the Compound (III) or its salt directly in the presence of a conventional condensing agent such as N,N-dicyclohexylcarbodiimide and the like. Among these activation methods, preferred activation method for the carboxy group of the Compound (II) into its activated form and preferred condensing agent as mentioned above are selected according to kinds of the carboxy protective group(s) of the Compound (II) and (III) and to the reaction conditions (e.g. the kinds of the reaction solvent, reaction temperature and so on).

This reaction is preferably carried out in a solvent such as methylene chloride, chloroform, tetrahydrofuran, dioxane, ethyl acetate, methanol, ethanol, water or the like under at $-20°$ C. to at ambient temperature and the reaction in the presence of a condensing agent is usually carried out in an anhydrous, but not critical conditions.

(2) Process 2: Elimination of protective group(s) Compound (Iᵃ)→Compound (Iᵇ)

This process relates to a method for preparing Compound (Iᵇ) or its salt by subjecting Compound (Iᵃ) or its salt to elimination reaction of protective group(s) of protected carboxy for $R_a^3$ and (or) $R^6$, and (or) amino protective group for $R_a^7$, detailed explanation for which is as follows:

Process 2-1: Elimination of an amino protective group for $R^7$

This process can be applied to case that the amino protective group for $R^7$ reveals a chemically different behavior from that of the acyl group for $R^1$ against each kind of the elimination methods to be employed, that is, the case that the amino protective group can be eliminated, but the acyl group for $R^1$ is not eliminated according to the elimination method as employed.

This reaction is carried out by conventional methods such as catalytic reduction method, liquidammoniaalkalimetal method, acid method, zinc acid method, base method, hydrazine method and the like. Among these methods, preferred one is selected according to kind of the amino protective group for $R^7$, and also to the chemically different behavior of said amino protective group from the acyl for $R^1$ as explained above.

Among the above elimination methods, an acid method is employed as the most convenient and conventional one and said method is explained as follows:

This reaction is conventionally carried out in a solvent such as methylene chloride, chloroform, acetic acid, water and the like in the presence of inorganic or organic acid such as trifluoroacetic acid, formic acid, p-toluenesulfonic acid, hydrochloric acid, hydrobromic acid and the like, and anisole is preferably added thereto.

Among the exemplified acid, trifluoroacetic acid and formic acid are also used as the solvent.

This reaction is usually carried out under cooling to an ambient temperature (for example, $-78°$ C. to at ambient temperature).

Process 2-2: Elimination of carboxy protective group of protected carboxy for $R_a{}^3$ and $R^6$ The reaction for elimination of protective group of the protected carboxy group is carried out by a conventional method such as hydrolysis and reduction or the like, details of which are explained in the following.

(i) For hydrolysis which refers to the same meaning as solvolysis including, for example, acidolysis, alcoholysis, aminolysis, hydroxinolysis, etc.:

Hydrolysis is preferably carried out in the presence of an acid or base.

Suitable acid includes an inorganic acid (e.g. hydrochloric acid, hydrobromic acid, hydrofluoric acid, sulfuric acid, etc.), an organic acid (e.g. formic acid, acetic acid, trifluoroacetic acid, propionic acid, benzenesulfonic acid, p-toluenesulfonic acid, etc.), boron trifluoride etherate, an acidic ion exchange resin and the like.

Suitable base includes an inorganic base such as alkali or alkaline earth metal hydroxide or the corresponding carbonate or bicarbonate (e.g. sodium hydroxide, potassium hydroxide, sodium carbonate, potassium carbonate, lithium carbonate, sodium bicarbonate, calcium hydroxide, magnesium hydroxide, etc.), ammonium hydroxide or the like; an organic base such as an alkoxide or phenoxide of the above metal (e.g. sodium ethoxide, sodium methoxide, lithium phenoxide, etc.), an amine such as mono-, di- or trialkylamine (e.g. methylamine, ethylamine, propylamine, isopropylamine, butylamine, N,N-dimethyl-1,3-propanediamine, trimethylamine, triethylamine, etc.), unsubstituted mono- or di-substituted arylamine (e.g. aniline, N-methylaniline, N,N-dimethylaniline, etc.), a heterocyclic base (e.g. pyrrolidine, morpholine, N-methylmorpholine, N-methylpiperidine, N,N'-dimethylpiperazine, pyridine, etc.), hydrazines (e.g. hydrazine, methylhydrazine, ethylhydrazine, etc.) or the like; a basic ion-exchange resin and the like.

The hydrolysis is preferably conducted under somewhat milder conditions such as cooling or warming and usually in a solvent which does not have adverse influence to the reaction, e.g. water, a hydrophilic solvent such as alcohol (e.g. methanol, ethanol, propanol, etc.), acetone, N,N-dimethylformamide, tetrahydrofuran, dioxane, dimethylsulfoxide, etc. or a mixture thereof, and other hydrophobic solvent such as benzene, diethylether, etc. may also be used as a solvent. A liquid abovementioned acid or base can also be used as solvent.

(ii) For reduction:

Reduction, including chemical reduction and catalytic reduction, is carried out in a conventional manner.

Suitable reducing agents to be used in chemical reduction are a metal (e.g. tin, zinc, iron, etc.), or a combination of such metal and/or metallic compound (e.g. chromous chloride, chromous acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum platinum black, colloidal platinum, platinum oxide or platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) or the like.

The reduction is usually carried out in a solvent. A suitable solvent to be used may be e.g. water, alcohol (e.g. methanol, ethanol, propanol, etc.) and other conventional organic solvent or a mixture thereof. Additionally, the afore-mentioned liquid acids to be used in chemical reduction can also be used as solvent. Further, a suitable solvent to be used in catalytic reduction may be, e.g. the above-mentioned solvent, and other conventional solvent, such as diethyl ether, dioxane, tetrahydrofuran etc., or a mixture thereof.

The reaction is preferably carried out under somewhat milder conditions such as cooling or warming.

Process 2-3: Removal of hydrozino group

A protective group of a protected carbazoyl of the formula: —CONHNHY (wherein Y is hydrogen or an amino protective group) can be removed by subjecting Compound ($I^a$) at first to the reaction of Process 2-1 for eliminating an amino protective group (i.e. Y) to give —CONHNH$_2$ group and then subjecting the reaction product to the reaction of this step to give —COOH group, and particular of this reaction step is as follow.

The reaction of this step is carried out in a conventional manner by treating the Compound ($I^a$) with a conventional oxidizing agent which is capable of oxidizing a group of the formula: —CONHNH$_2$ to form into a group of the formula: —COOH and accordingly preferred example of such an oxidizing agents may be halogen such as iodine, bromine etc., perhalogenic acid such as periodic acid or its salt (e.g. sodium salt, potassium salt, etc.), perchloric acid, etc., N-haloimide such as N-bromosuccinimide, etc., lead tetraacetate, hydrogen peroxide or its salt (e.g. nickel peroxide, etc.), metal oxide such as mercuric oxide, manganese dioxide, nickel peroxide, etc., cupric compound (e.g. cupric acetate, cupric sulfate, etc.) and the like.

This reaction is usually carried out in a solvent such as water, acetic acid, methanol, ethanol, tetrahydrofuran, dioxane and the like and a mixture thereof, which should be appropriately selected in accordance with the kind of oxidizing agent to be used.

This reaction is usually carried out under cooling to at ambient temperature, or under reflux.

Among these methods for elimination of protective groups, preferred one and appropriate combination methods are to be selected according to kinds of the protective groups of carboxy group and amino protective group to be removed off.

It is noted that this process includes the following cases of elimination of protective groups of protected carboxy and amino protective group, that is, one case that all of the carboxy protective groups for $R_a^3$ and $R^6$ and the amino protective group for $R^7$ in the Compound ($I^a$) are simultaneously removed by a method to be employed to the reaction, and the other case that the carboxy protective groups and the amino protective group are sequentially and stepwise removed by a method which is appropriately selected according to the kinds of the protective group to be removed.

As to Process 2 for elimination of protective group(s) (i.e. Process 2-1 and 2-2 and 2-1), the followings are to be noted. That is, in case that acyl for $R^1$ has one or more protective group(s) for hydroxy, amino and (or) carboxy, such an amino protective group and carboxy protective group among said protective group may be simultaneously removed in this process, and such a hydroxy protective group such as alkanoyl (e.g. acetyl, etc.) may be previously removed by subjecting the compound ($I^a$) to elimination reaction of hydroxy protective group in a conventional manner such as reduction as illustrated in the Process 2-2.

(3) Process 3: Deacylation Compound ($I^c$)→Compound ($I^d$)

This process relates to a method for preparing Compound ($I^d$) or its salt by subjecting Compound ($I^c$) or its salt to a deacylation reaction of an acyl group for $R_a^1$.

This reaction is carried out substantially in the same manner as Process 2-1.

It is noted that in this reaction carboxy protective groups of protected carboxy for $R^3$ and $R^6$, and (or) an amino protective group for $R^7$ may be simultaneously removed, and such a case is included in this process.

The starting compounds (II) and (III) include known compounds (e.g. European Patent publication No. 11283) and new compounds. Said new compound can be prepared, for example, by methods as described below.

(1) Process $1^s$:

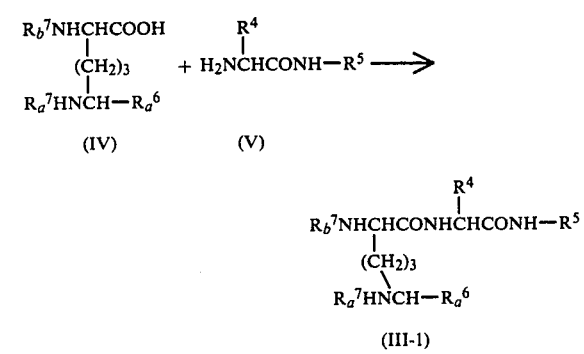

(2) Process $2^s$:

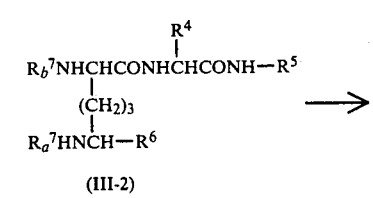

-continued

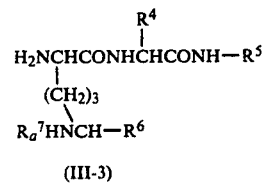

(3) Process $3^s$:

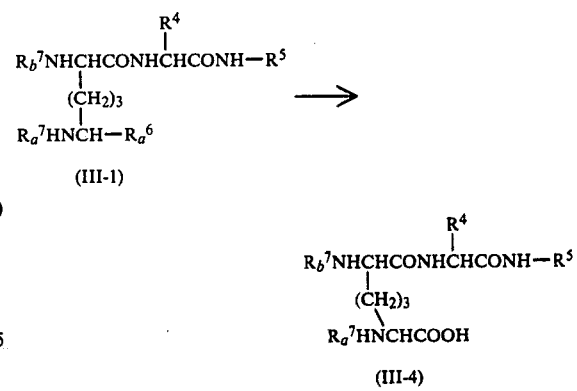

In the above formulae, $R_a^6$ is protected carboxy, $R_b^7$ is an amino protective group, and $R^4$, $R^5$, $R^6$, $R^7$ and $R_a^7$ are each as defined above.

(1) Process $1^s$: Compound (IV)+Compound (V)→Compound (III-1)

This process relates to a method for preparing Compound (III-1) or its salt by reacting Compound (IV) or its salt with Compound (V) or its salt.

This reaction is carried out substantially in the same manner as Process 1.

(2) Process $2^s$: Compound (III-2)→Compound (III-3)

This process relates to a method for preparing Compound (III) or its salt by subjecting Compound (III-2) or its salt to elimination reaction of an amino protective group for $R_b^7$.

This reaction is carried out substantially in the same manner as Process 2-1.

(3) Process $3^s$: Compound (III-1)→Compound (III-4)

This process relates to a method for preparing Compound (III-4) or its salt by subjecting Compound (III-1) or its salt to elimination reaction of carboxy protective group of protected carboxy for $R_a^6$.

This reaction is carried out substantially in the same manner as Process 2-2.

As to the object compound (I) and starting compounds (II) and (III) which are prepared according to the aforementioned Processes, it is to be noted that each of said compounds includes one or more stereoisomers which is due to the asymmetric carbon atoms in their molecule and all of such isomers are included within the scope of this invention.

The new peptide (I) and its pharmaceutically acceptable salts of this invention have been found to possess protective efficacy in experimental infection.

Accordingly, the new peptide (I) and its pharmaceutically acceptable salts are useful for the therapeutic treatment of infectious diseases caused by pathogenic microorganism, especially gram-negative bacteria and gram-positive bacteria and fungi.

PROTECTIVE EFFICACY IN EXPERIMENTAL INFECTION IN MICE

In determining the protective efficacy against experimental infections in mice, the test compound was dissolved in and diluted with sterile saline to provide prescribed concentrations of drug.

Male ICR-strain mice, aged 4 weeks were used in groups of ten mice. E. coli 22 was cultivated overnight at 37° C. on trypticase soy agar and then were suspended in a sterile to obtain microbial cell concentration of $2.6 \times 10^9$ CFU/ml. Mice were inoculated intraperitoneally with $5.8 \times 10^7$ CFU/mouse. Each of the test drugs was given intraperitoneally in various doses to a group of ten mice four days before challenge.

Survival percent were found from the number of the surviving animals after three days of injection. Results are shown in Table.

| Test Compound (Example No.) | Survival (%) Dose 0.1 mg/kg | Dose 0.01 mg/kg | Control |
|---|---|---|---|
| Example 1 (Step 3) | 40 | — | 0 |
| Example 4 (Step 3) | 40 | — | 0 |
| Example 5 (Step 2) | 90 | — | 0 |
| Example 7 (Step 4) | 30 | — | 0 |
| Example 8 (Step 4) | 60 | 40 | 0 |
| Example 11 (Step 4) | 20 | — | 0 |
| Example 12 (Step 4) | 50 | 80 | 0 |

Further, compounds (II) and (III) are useful as an intermediate for preparing compound (I) having biologically active properties as mentioned above.

The pharmaceutical composition of this invention can be used in the form of a pharmaceutical preparation, for example, in solid, semisolid or liquid form, which contains an active substance of this invention in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, collidal silica, potato starch, urea and other carriers suitable for use in manufacturing preparations, in solid, semisolid, or liquid form, and in addition auxiliary, stabilizing, thickening and coloring agents and perfumes may be used. The pharmaceutical compositions can also contain preservative or bacteriostatic agents to keep the active ingredient in the desired preparations stable in activity. The active object compound is included in the pharmaceutical composition in an amount sufficient to produce the desired therapeutic effect upon the process or condition of diseases.

For applying this composition to humans, it is preferable to apply it by intravenous, intramuscular or oral administration. While the dosage or therapeutically effective amount of the object compound of this invention varies from and also depends upon the age and condition of each individual patient to be treated, a daily dose of about 0.001–100 mg of the active ingredient/kg of a human being or an animal is generally give for treating diseases, and an average single dose of about 50 mg, 100 mg, 250 mg, and 500 mg is generally administered.

The following examples are given for purpose of illustrating this invention.

In the following examples, starting compounds and object compounds are expressed by using the following abbreviations:

| | |
|---|---|
| Lac | Lactoyl |
| Ala | Alanyl |
| Glu | Glutamyl |
| Gly | Glycyl |
| DAP | α, ε-Diaminopimelyl |
| Z | benzyloxycarbonyl |
| Boc | t-butoxycarbonyl |
| Bzl | Benzyl |
| Ac | acetyl |
| Su | N—hydroxysuccinimide |

PREPARATION 1

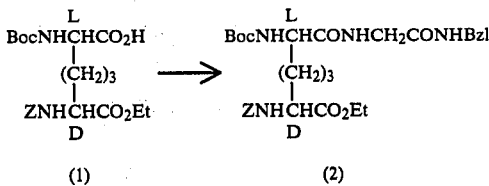

To a solution of Boc-(L)-Z-(D)-mesoDAP-(D)-OEt (1) (1.5 g) and triethylamine (0.33 g) in dichloromethane (10 ml) was added isobutyloxycarbonylchloride (0.45 g) at −22° C. with stirring. After stirring for 70 minutes a solution of glycine benzylamide trifluoroacetate (0.92 g) and triethylamine (0.33 g) in dichloromethane (10 ml) was added to the reaction mixture at −22° C. with stirring. After stirring at −22 ∼ −15° C. for 40 minutes, the mixture was allowed to reach to room temperature. The solvent was evaporated and the residue was dissolved in ethyl acetate (30 ml) and water (20 ml). The organic layer was washed with aqueous sodium bicarbonate (15 ml) and water (15 ml×3), dried over magnesium sulfate and evaporated to give a powder, which was washed with ether to give Boc-(L)-Z-(D)-mesoDAP-(L)-GlyNHBzl-(D)-OEt (2) (1.75 g). m.p. 127°–128° C.

NMR (CDCl₃) δ 1.28 (3H, t, J=7 Hz), 1.40 (9H, s), 1.3–2.0 (6H, m), 3.95 (2H, d, J=6 Hz), 4.20 (2H, q, J=7 Hz), 4.43 (2H, d, J=6 Hz), 5.10 (2H, s), 5.1∼5.8 (2H, m), 7.27 (5H, s), 7.33 (5H, s).

IR (Nujol): 3300, 1735, 1690, 1635, 1280, 1165 cm⁻¹.

PREPARATION 2

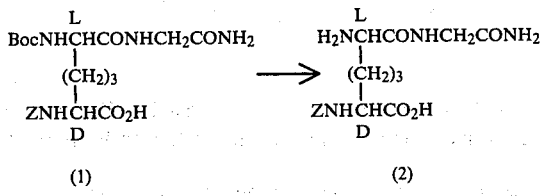

Boc-(L)-Z-(D)-mesoDAP-(L)-GlyNH₂ (1) (1.41 g) was dissolved in trifluoroacetic acid (10 ml) and stirred for 30 minutes at room temperature. After the solvent was removed in vacuo, the residue was dissolved in water. The solution was neutralized with 1M sodium carbonate and put on a column of HP-20 (30 ml). After washing with water (100 ml), the column was eluted with 70% aqueous methanol and the eluate was evaporated to give a powder, which was washed with ethanol to yield Z-(D)-mesoDAP-(L)-GlyNH₂ (2) (0.73 g), m.p. 185°–187° C.

IR (Nujol): 3480, 3320, 3260, 1700, 1665, 1610, 1550, 1510 cm⁻¹. NMR (D₂O): δ 1.2–2.0 (6H, m), 3.8–4.1 (4H, m), 5.08 (2H, s), 7.40 (5H, s).

PREPARATION 3

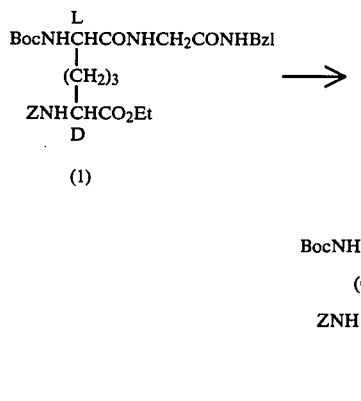

To a solution of Boc-(L)-Z-(D)-mesoDAP-(L)-GlyNHBzl-(D)-OEt (1) (1.60 g) in methanol (10 ml) was added 2M potassium carbonate aqueous solution (4 ml) at 0° C. After stirring for 6.5 hours at room temperature, the solution was left in a refrigerator overnight. The solution was acidified with 10% hydrochloric acid (20 ml) and extracted with ethyl acetate (30 ml). The organic layer was washed with water (15 ml×2) and dried over magnesium sulfate. The solvent was evaporated and the residue was pulverized with diethyl ether (20 ml) to give Boc-(L)-Z-(D)-mesoDAP-(L)-GlyNHBzl (2) (1.44 g). m.p. 146°–148° C.

IR (Nujol): 3410, 3350, 3320, 3300, 1735, 1705, 1690, 1600 cm⁻¹. NMR (CDCl₃+CD₃OD): δ 1.42 (9H, s), 1.2–2.0 (6H, m), 3.95 (2H, m), 3.9–4.5 (2H, m), 4.45 (2H, s), 5.13 (2H, s), 7.30 (5H, s), 7.37 (5H, s).

PREPARATION 4

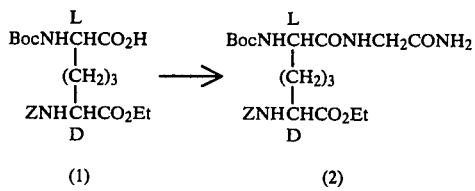

Boc-(L)-Z-(D)-mesoDAP-(D)-OEt-(L)-GlyNH₂ (2) was prepared in a similar manner to that of Preparation 1.

IR (Nujol): 3310, 3100, 1720 (shoulder), 1690, 1670, 1550, 1510, 1165 cm⁻¹. NMR (CDCl₃): δ 1.23 (3H, t, J=7 Hz), 1.40 (9H, s), 1.3–2.1 (6H, m), 3.8–4.5 (4H, m), 4.17 (2H, q, J=7 Hz), 5.07 (2H, s), 5.4–6.8 (5H, m), 7.30 (5H, s). m.p. 100°–101° C.

PREPARATION 5

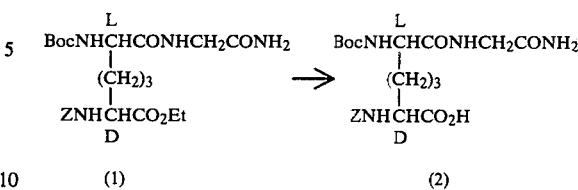

Boc-(L)-Z-(D)-mesoDAP-(L)-GlyNH₂ (2) was prepared in a similar manner to that of Preparation 3. m.p. 80°–83° C. (dec.)

IR (Nujol): 3300, 1680 (broad), 1525 cm⁻¹. NMR (CD₃OD): δ 1.47 (9H, s), 1.5–2.0 (6H, m), 3.87 (2H, s), 3.8–4.3 (2H, m), 5.13 (2H, s), 7.37 (5H, s)

PREPARATION 6

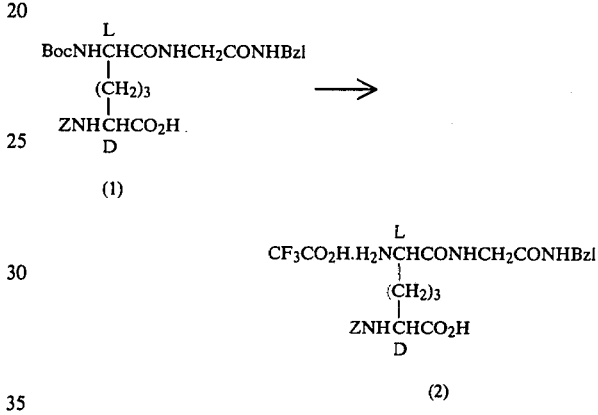

Boc-(L)-Z-(D)-mesoDAP-(L)-GlyNHBzl (1.36 g) was dissolved in trifluoroacetic acid (10 ml). After stirring for 30 min. at room temperature, the mixture was evaporated in vacuo. The residue was pulverized with ether to give Z-(D)-mesoDAP-(L)-GlyNHBzl.CF₃COOH (2) (1.43 g). m.p. 185°–188° C.

IR (Nujol): 3300, 1700, 1640, 1600, 1540 cm⁻¹ NMR (CD₃OD): δ 1.5–2.2 (6H, m), 3.8–4.5 (2H, m), 4.00 (2H, s), 4.42 (2H, s), 5.12 (2H, s), 7.30 (5H, s), 7.35 (5H, s).

PREPARATION 7

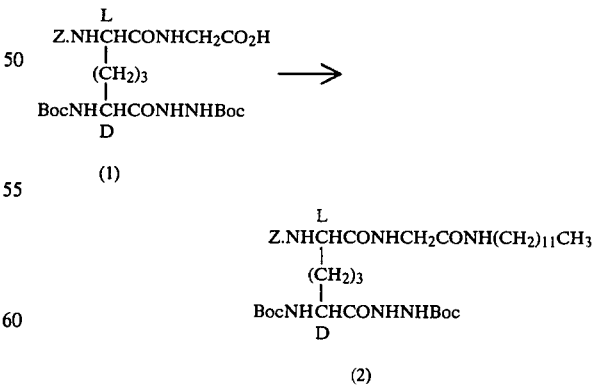

To a solution of Z-(L)-Boc-(D)-mesoDAP-(L)-Gly-(D)-NHNHBoc (1) (1.7 g) and triethylamine (0.29 g) in dichloromethane (10 ml) was added iso-butyloxycarbonylchloride (0.39 g) with stirring at −22° C. After stirring for 45 minutes at −19° C., a solution of laurylamine (0.53 g:2.9 mM) in dichloromethane (10 ml) was added to the mixture at −20° C. The mixture was stirred at −17° C. for 2 hours, then the mixture was allowed to reach to room temperature.

After evaporation, the residue was dissolved in ethyl acetate (30 ml) and water (15 ml). The organic layer was washed with 10% hydrochloric acid (15 ml), water (15 ml), dilute sodium bicarbonate (15 ml) and water (15 ml×2) and dried over magnesium sulfate. The solvent was removed in vacuo. The residue was put on a column of silicagel (Merk). The column was eluted with chloroform-methanol (20:1 v/v) and the eluate was evaporated to give residues, which were treated with n-hexane to give Z-(L)-Boc-(D)-mesoDAP-(L)-GlyNHlauryl-(D)-NHNHBoc (2). m.p. 78°–80° C.

IR (Nujol): 3300, 1680 (broad), 1520, 1240, 1160 cm$^{-1}$. NMR (CDCl$_3$): δ 0.7–1.0 (3H, m), 1.0–2.0 (44H, m), 3.0–3.3 (2H, m), 3.82 (2H, m), 4.0–4.3 (2H, m), 5.04 (2H, s), 5.5 (1H, s), 6.2 (1H, s), 6.8 (1H, s). 6.96 (1H, s), 7.27 (5H, s), 7.5 (1H, s), 9.1 (1H, s)

PREPARATION 8

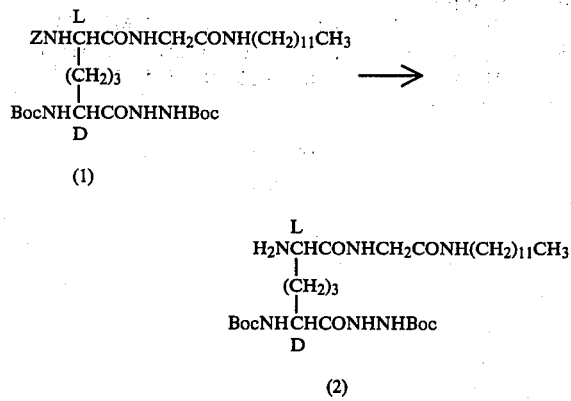

A solution of Z-(L)-Boc-(D)-mesoDAP-(L)-GlyNH-lauryl-(D)-NHNHBoc (1) (1.80 g) in 90% aqueous methanol (45 ml) was hydrogenolyzed in the presence of 10% palladium charcoal (0.2 g). After the catalyst was removed, the solvent was evaporated in vacuo to give a residue which was treated with iso-propylether to give Boc-(D)-mesoDAP-(L)-GlyNHlauryl-(D)-NHNHBoc (2)) 1.27 g). m.p. 55°–58° C.

IR (Nujol): 3320, 1680 (broad), 1530, 1170 cm$^{-1}$. NMR (CDCl$_3$): δ 0.7–1.0 (3H, m), 1.0–2.0 (44H, m), 3.0–3.5 (2H, m), 3.85 (2H, s), 3.8–4.2 (2H, m), 5.5 (1H, s), 6.70 (1H, s), 8.00 (1H, s).

PREPARATION 9

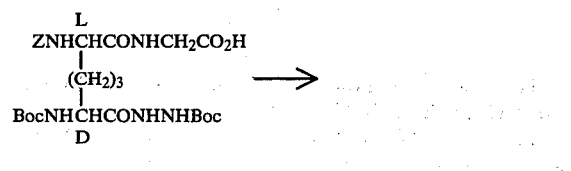

Z-(L)-Boc-(D)-mesoDAP-(L)-GlyNHhexyl-(D)-NHNHBoc (2) was prepared in a similar manner to that of Preparation 7. m.p. 91°–93° C.

IR (Nujol): 3350, 1690 (broad), 1525, 1250, 1165 cm$^{-1}$. NMR (CDCl$_3$): δ 0.7–1.1 (3H, m), 1.0–2.1 (32H, m), 2.1–2.8 (2H, m), 3.0–3.5 (2H, m), 3.7–4.0 (2H, m), 4.0–4.6 (2H, m), 5.10 (2H, s), 5.3–5.6 (1H, m), 6.0–6.5 (1H, m), 6.6–7.1 (2H, m), 7.33 (5H, s), 7.5–7.8 (1H, m), 8.9–9.3 (1H, m).

PREPARATION 10

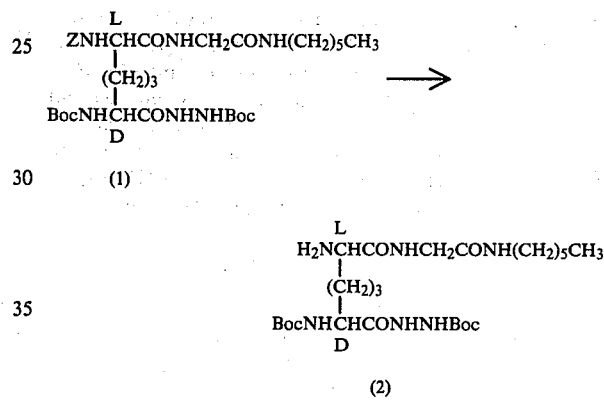

Boc-(D)-mesoDAP-(L)-GlyNHhexyl-(D)-NHNHBoc (2) was prepared in a similar manner to that of Preparation 8. m.p. 68°–70° C.

IR (Nujol): 3280, 1670, 1520, 1240, 1160 cm$^{-1}$. NMR (CDCl$_3$): δ 0.7–1.0 (3H, m), 1.0–2.1 (32H, m), 3.0–3.6 (2H, m), 3.8–4.2 (2H, m), 4.2–5.0 (2H, m), 5.7 (2H, d, J=7 Hz), 6.7–7.0 (1H, m), 8.0–8.3 (1H, m).

EXAMPLE 1

(1) Step 1

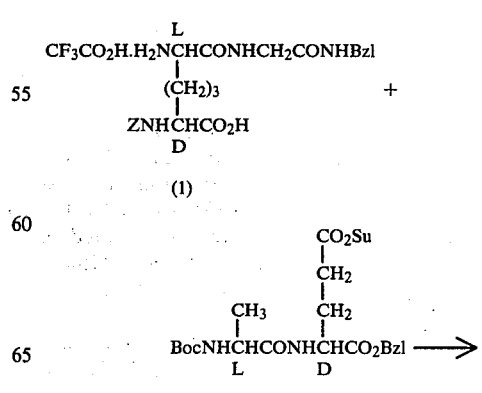

-continued

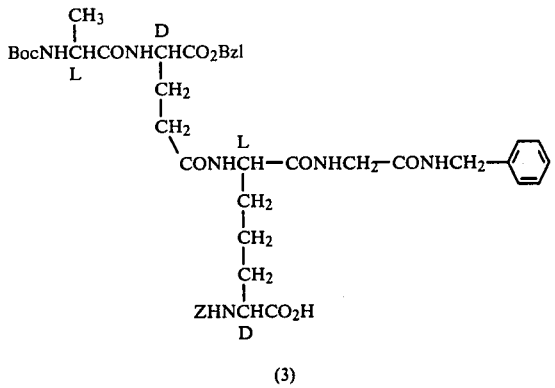

(3)

To a solution of Z-(D)-mesoDAP-(L)-GlyNHBzl.CF₃COOH (1) (0.53 g) and triethylamine (0.18 g) in 80% aqueous acetone (6 ml) was added a solution of Boc-L-Ala-D-Glu(α-OBzl)-γ-OSu (2) (0.49 g) in acetone (5 ml) with stirring at 0° C. After stirring at 0° C. for 1 hour and at room temperature overnight, the mixture was evaporated and the residue was dissolved in ethyl acetate (20 ml) and water (15 ml). The organic layer was washed with water (15 ml×2), 10% hydrochloric acid (10 ml) and water (10 ml×2) and dried over magnesium sulfate. The solvent was removed in vacuo and the residue was pulverized with diethylether to yield Boc-L-Ala-γ-D-Glu(α-OBzl)-(L)-mesoDAP-(D)-Z-(L)-GlyNHBzl (3) (0.50 g). m.p. 116°–117° C.

IR (Nujol): 3300, 1740, 1690, 1650, 1635, 1540, 1165 cm⁻¹. NMR (CDCl₃+CD₃OD): δ 1.30 (3H, d, J=7 Hz), 1.45 (9H, s), 1.5–2.0 (6H, m), 9.0–2.5 (4H, m), 3.8–4.5 (6H, m), 5.10 (2H, s), 5.15 (2H, s), 7.23 (5H, s), 7.33 (10H, s).

(2) Step 2

Compound (3) ⟶

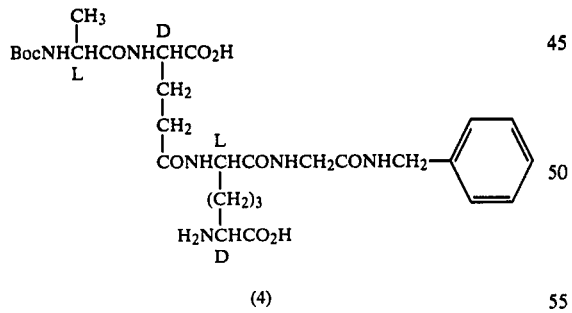

(4)

A solution of Boc-L-Ala-γ-D-Glu(α-OBzl)-(L)-Z-(D)-mesoDAP-(L)-GlyNHBzl (3) (0.46 g) in 80% aqueous methanol (25 ml) was hydrogenolyzed in the presence of 10% palladium charcoal (0.15 g). After the catalyst was removed, the solvent was evaporated in vacuo. Lyophilization gave Boc-L-Ala-γ-D-Glu(α-OH)-(L)-mesoDAP-(L)-GlyNHBzl (4) (0.30 g). m.p. 145°–147° C.

IR (Nujol): 3300, 1650, 1520 cm⁻¹. NMR (D₂O): δ 1.32 (3H, d, J=8 Hz), 1.40 (9H, s), 1.5–2.5 (10H, m), 3.72 (1H, t, J=6 Hz), 3.94 (2H, s), 3.9–4.4 (3H, m), 4.40 (2H, d, J=2 Hz), 7.32 (5H, d, J=2 Hz).

(3) Step 3

Compound (4) ⟶

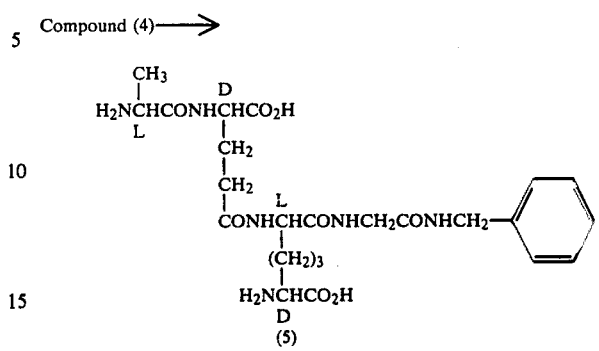

(5)

Boc-L-Ala-γ-D-Glu(α-OH)-(L)-mesoDAP-(L)-GlyNHBzl (4) (0.29 g) was dissolved in trifluoroacetic acid (10 ml) and stirred for 30 minutes at room temperature. After the solvent was removed in vacuo, the residue was dissolved in water and put on a column of HP-20 (30 ml). After washing with water (200 ml), the column was eluted with 50% aqueous methanol. The eluate was concentrated and lyophilized to give L-Ala-γ-D-Glu(α-OH)-(L)-mesoDAP-(L)-GlyNHBzl (5) (0.19 g). mp 173°–175° C.

IR (Nujol): 3250, 1640, 1540 cm⁻¹. NMR (D₂O): δ1.48 (3H, d, J=8 Hz), 1.5–2.4 (10H, m), 3.64 (1H, m), 3.90 (2H, s), 3.9–4.4 (3H, m), 4.36 (2H, d, J=2 Hz), 7.28 (5H, d, J=2 Hz).

EXAMPLE 2

(1) Step 1

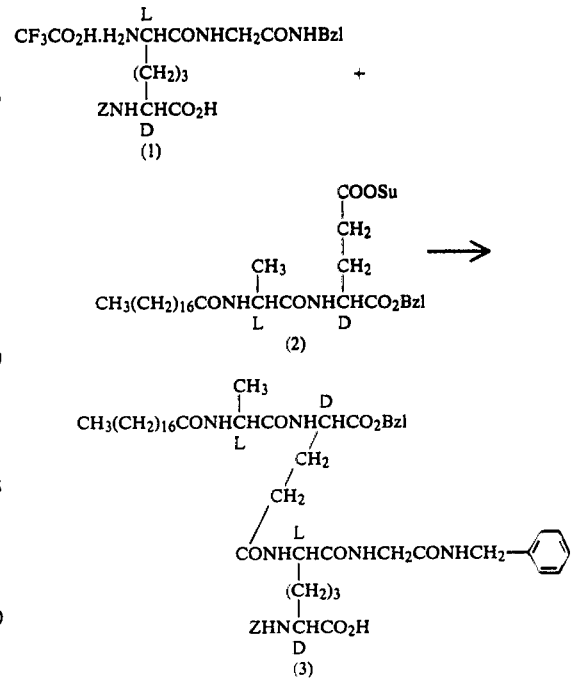

To a solution of Z-(D)-mesoDAP-(L)-GlyNHBzl.CF₃COOH (1) (0.35 g) and triethylamine (0.12 g; 1.2 mM) in 80% aqueous acetone (6 ml) was added a solution of stearoyl-L-Ala-D-Glu(α-OBzl)-γ-OSu (2) (0.40 g) in acetone (5 ml) and 1,4-dioxane (5 ml)

with stirring at 0° C. Stirring was continued overnight at room temperature. After evaporation the residue was washed with 10% hydrochloric acid (15 ml) and ethyl acetate (10 ml). The resulting powder was washed with 10% hydrochloric acid (10 ml×2), water (10 ml×2) and ethyl acetate (10 ml) to give stearoyl-L-Ala-γ-D-Glu(α-OBzl)-(L)-Z-(D)-mesoDAP-(L)-GlyNHBzl (3) (0.49 g). mp. 170°–171° C.

IR (Nujol): 3300, 1740, 1650, 1630, 1540 cm$^{-1}$. NMR (CDCl$_3$+CO$_3$OD): δ0.8–1.0 (3H, m), 1.0–2.3 (45H, m), 3.90 (2H, s), 5.10 (2H, s), 5.18 (2H, s), 7.23 (5H, s), 7.33 (10H, s).

(2) Step 2

Compound (3)⎯⎯→

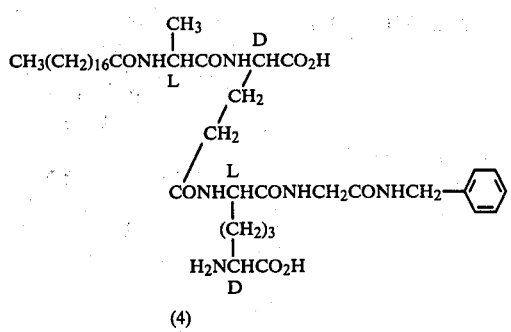

(4)

A solution of stearoyl-L-Ala-γ-D-Glu(α-OBzl)-(L)-Z-(D)-mesoDAP-(L)-GlyNHBzl (3) (0.44 g) in acetic acid (20 ml) was hydrogenolyzed in the presence of 10% palladium charcoal (0.1 g). After the catalyst was removed, the solvent was evaporated in vacuo and the residue was washed with methanol (20 ml) to yield stearoyl-L-Ala-γ-D-Glu(α-OH)-(L)-mesoDAP-(L)-GlyNHBzl (4) (0.14 g). mp 166°–171° C. (dec.).

IR (Nujol): 3280, 1720(shoulder), 1630, 1520 cm$^{-1}$. NMR (CF$_3$CO$_2$h): δ0.8–1.1 (3H, m), 1.1–3.0 (45H, m), 4.0–5.1 (8H, m), 7.40 (5H, s).

EXAMPLE 3

(1) Step 1

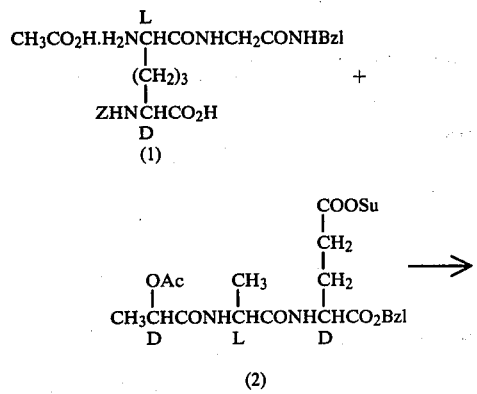

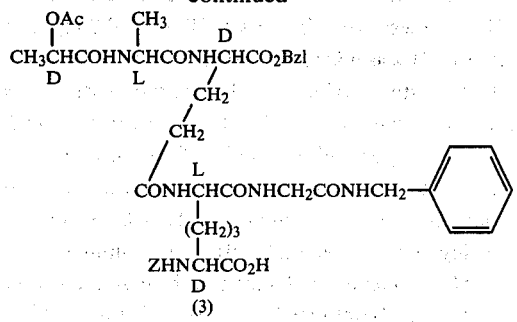

(3)

D-Lac(OAc)-L-Ala-γ-D-Glu(α-OBzl)-(L)-Z-(D)-mesoDAP-(L)-GlyNHBzl (3) was prepared in a similar manner to that of step 1 of Example 1. mp 83°–86° C.

IR (Nujol): 3300, 1730, 1650, 1530, 1230 cm$^{-1}$. NMR (CDCl$_3$+CD$_3$OD): δ1.35 (3H, d, J=7 Hz), 1.43 (3H, d, J=7 Hz), 1.3—2.3 (10H, m), 2.67 (3H, s), 5.08 (2H, s), 5.13 (2H, s), 7.20 (5H, s), 7.33 (10H, s).

(2) Step 2

Compound (3)⎯⎯→

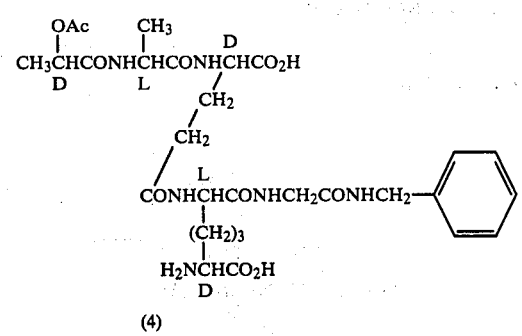

(4)

D-Lac(OAc)-L-Ala-γ-D-Glu(α-OH)-(L)-mesoDAP-(L)-GlyNHBzl (4) was prepared in a similar manner to that of step 2 of Example 1. mp. 133°–135° C.

IR (Nujol): 3300, 1730, 1650, 1540, 1240 cm$^{-1}$. NMR (D$_2$O): δ1.36 (3H, d, J=8 Hz), 1.44 (3H, d, J=7 Hz), 1.5–2.5 (10H, m), 2.10 (3H, s), 3.68 (1H, m), 3.92 (2H, s), 4.0–4.3 (3H, m), 4.38 (2H, d, J=2 Hz), 4.96 (1H, m), 7.28 (5H, d, J=2 Hz).

(3) Step 3

Compound (4)⎯⎯→

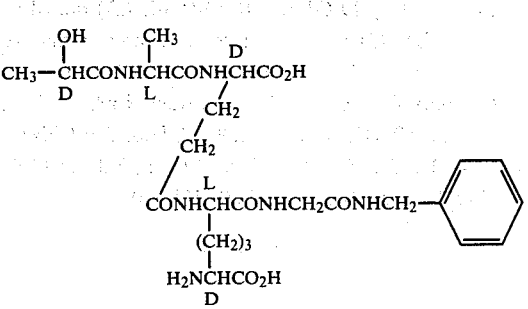

(5)

To a solution of D-Lac(OAc)-L-Ala-γ-D-Glu(α-OH)-(L)-mesoDAP-(L)-GlyNHBzl (4) (0.24 g) in methanol (5 ml) was added 2M potassium carbonate (0.5 ml) at 0° C. After stirring for 9 hours, the mixture was left in a refrigerator overnight. The mixture was acidified with 10% hydrochloric acid (1.5 ml) and the solvent was removed in vacuo. The residue was dissolved in water and put on a column of HP-20 (30 ml). After washing with water (150 ml), the column was eluted with 50% aqueous methanol and the eluate was concentrated and lyophilized to give D-Lac-L-Ala-γ-D-Glu(α-OH)-(L)-mesoDAP-(L)-GlyNHBzl (5) (0.19 g:82.6%). mp 148°–152° C.

IR (Nujol): 3300, 1720 (shoulder, 1620, 1530 cm$^{-1}$. NMR (D$_2$O): δ1.37 (3H, d, J=7 Hz), 1.40 (3H, d, J=7 Hz), 1.5–2.5 (10H, m), 3.77 (1H, m), 3.97 (2H, s), 4.1–4.5 (6H, m), 7.33 (5H, s).

EXAMPLE 4

(1) Step 1

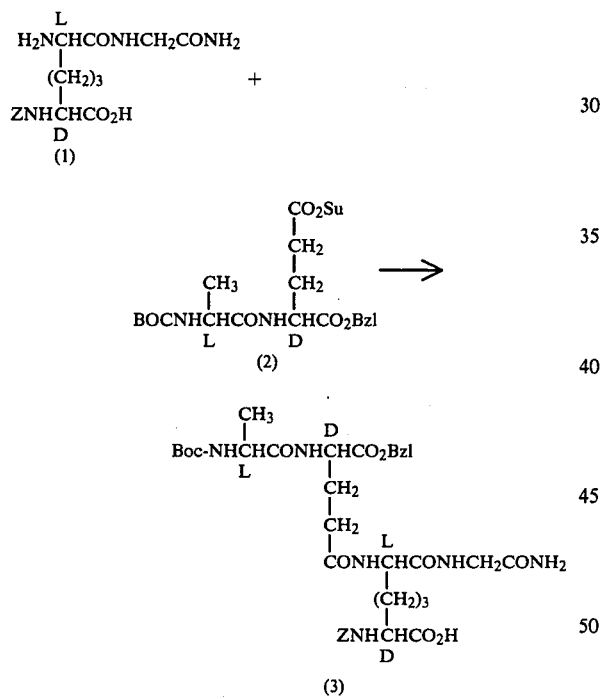

Boc-L-Ala-γ-D-Glu(α-OBzl)-(L)-Z-(D)-mesoDAP-(L)-GlyNH$_2$ (3) was prepared in a similar manner to that of Step 1 of Example 1. mp. 115°–117° C. (dec.).

IR (Nujol): 3300, 1720 (shoulder), 1690, 1650, 1530 cm$^{-1}$. NMR (CD$_3$OD): δ1.30 (3H, d, J=7 Hz), 1.43 (9H, s), 1.5–2.6 (10H, m), 3.70 (2H, s), 3.8–4.5 (4H, m), 4.97 (2H, s), 5.03 (2H, s), 7.20 (10H, s).

(2) Step 2

Compound (3) ⟶

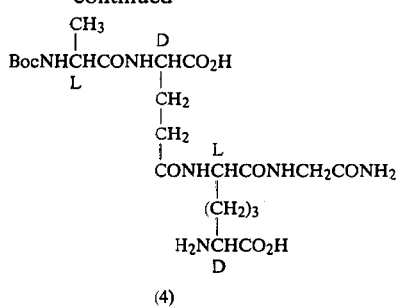

Boc-L-Ala-γ-D-Glu(α-OH)-(L)-mesoDaP-(L)-GlyNH$_2$ (4) was prepared in a similar manner to that of Step 2 of Example 1.

IR (Nujol): 3300, 1640 (broad), 1520 (broad) cm$^{-1}$. NMR (D$_2$O): δ1.43 (9H, s), 1.5–2.6 (13H, m), 3.77 (1H, m), 3.92 (2H, s), 4.0–4.5 (3H, m).

(3) Step 3

Compound (4) ⟶

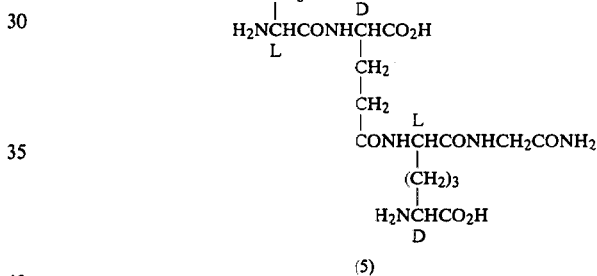

L-Ala-γ-D-Glu(α-OH)-(L)-mesoDAP-(L)-GlyNH$_2$ (5) was prepared in a similar manner to that of Step 2 of Example 1. mp 201°–208° C.

IR (Nujol): 3260, 1630 (broad) cm$^{-1}$. NMR (D$_2$O): δ1.54 (3H, d, J=7 Hz), 1.5–2.4 (10H, m), 3.74 (1H, m), 3.92 (2H, s), 3.9–4.4 (3H, m).

EXAMPLE 5

(1) Step 1

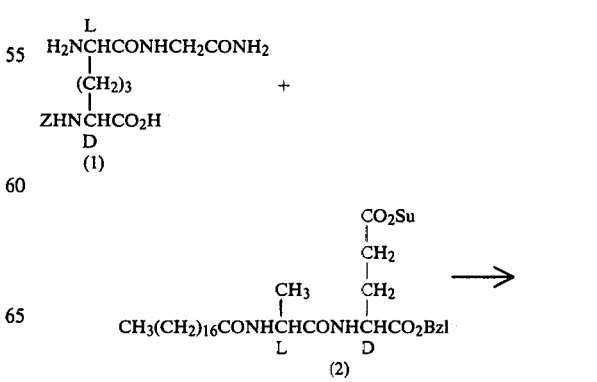

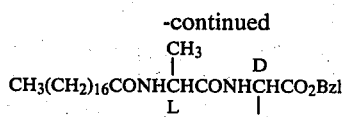

(3)

Stearoyl-L-Ala-γ-D-Glu(α-OBzl)-(L)-Z-(D)-mesoDAP-(L)-GlyNH₂ (3) was prepared in a similar manner to that of Step 1 of Example 2. mp 183°–186° C.

IR (Nujol): 3270, 1720, 1680, 1635, 1540 cm⁻¹. NMR (CD₃OD+CDCl₃): δ0.8–1.0 (3H, m), 1.1–2.5 (45H, m), 3.83 (2H, s), 3.8–4.5 (4H, m), 5.20 (2H, s), 5.27 (2H, s), 7.43 (10H, s).

(2) Step 2

Compound (3) ⟶

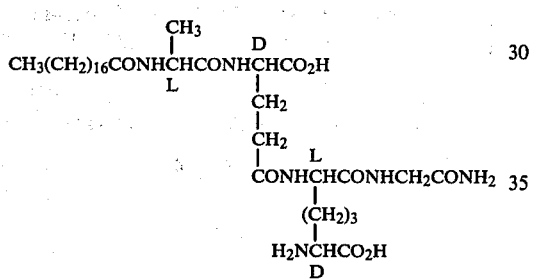

(4)

Stearoyl-L-Ala-γ-D-Glu(α-OH)-(L)-mesoDAP-(L)-GlyNH₂ (4) was prepared in a similar manner to that of Step 2 of Example 2. mp 140° C. (dec.).

IR (Nujol): 3300, 1720 (shoulder), 1630, 1540 cm⁻¹. NMR (N$_a$HCO₃+D₂O): δ0.6–1.0 (3H, m), 1.0–2.6 (45H, m), 3.70 (1H, m), 3.88 (2H, s), 4.0–4.5 (3H, m).

EXAMPLE 6

(1) Step 1

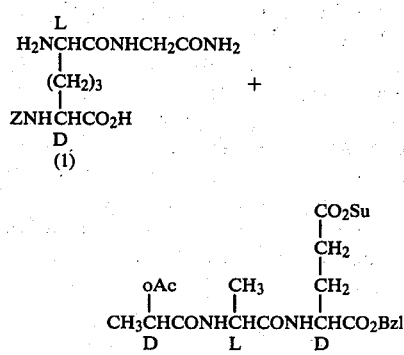

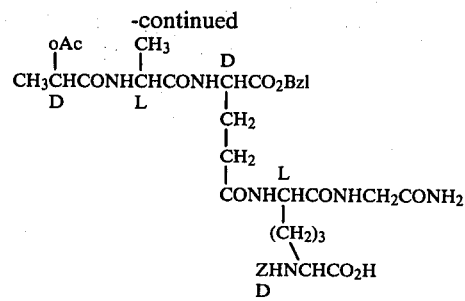

(3)

D-Lac(OAc)-L-Ala-γ-D-Glu(α-OBzl)-(L)-Z-(D)-mesoDAP-(L)-GlyNH₂ (3) was prepared in a similar manner to that of Step 1 of Example 3. mp. 161°–163° C.

IR (Nujol): 3280, 1725, 1640, 1535 cm⁻¹. NMR (CD₃OD): δ1.35 (3H, d, J=7 Hz), 1.43 (3H, d, J=7 Hz), 1.5–2.5 (10H, m), 2.08 (3H, s), 3.83 (2H, s), 4.0–5.0 (5H, m), 5.10 (2H, s), 5.17 (2H, s), 7.33 (10H, s).

(2) Step 2

Compound (3) ⟶

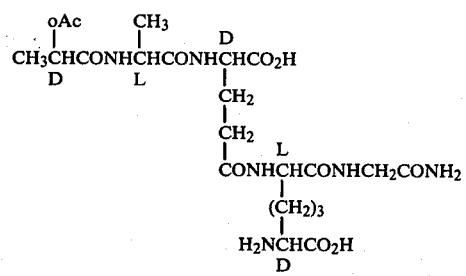

(4)

D-Lac(OAc)-L-Ala-γ-D-Glu(α-OH)-(L)-mesoDAP-(L)-GlyNH₂ (4) was prepared in a similar manner to that of Step 2 of Example 3. mp. 115°–118° C. (dec.)

IR (Nujol): 3280, 1650, 1530 cm⁻¹. NMR (D₂O): δ1.40 (3H, d, J=7 Hz), 1.45 (3H, d, J=7 Hz), 1.5–2.5 (10H, m), 2.13 (3H, s), 3.77 (1H, m), 3.90 (2H, s), 4.1–4.5 (3H, m), 5.03 (1H, q, J=7 Hz).

(3) Step 3

Compound (4) ⟶

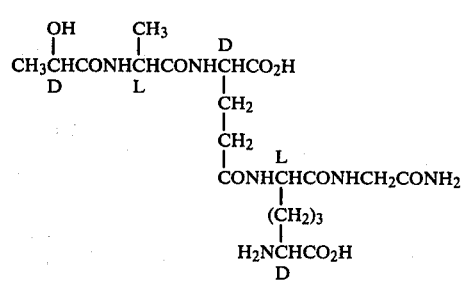

(5)

D-Lac-L-Ala-γ-D-Glu(α-OH)-(L)-mesoDAP-(L)-GlyNH₂ (5) was prepared in a similar manner to that of Step 3 of Example 3. mp. 197°–203° C. (dec.).

IR (Nujol): 3250, 1720 (shoulder), 1650 (broad), 1530 (broad). NMR (D$_2$O): δ1.34 (3H, d, J=7 Hz), 1.40 (3H, d, J=7 Hz), 1.5–2.5 (10H, m), 3.70 (1H, m), 3.84 (2H, s), 4.0–5.0 (4H, m).

EXAMPLE 7

(1) Step 1

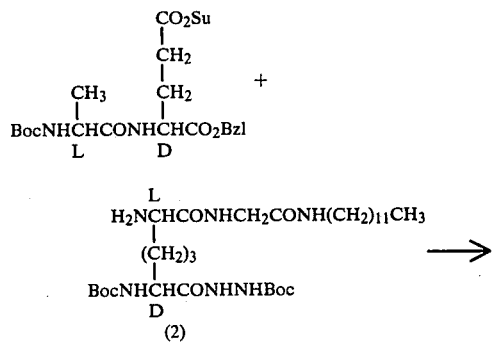

(2)

Boc-L-Ala-γ-D-Glu(α-OBzl)-(L)-Boc-(D)-mesoDAP-(L)-GlyNHlauryl-(D)-NHNHBoc (3) was prepared in a similar manner to that of Step 1 of Example 1. mp. 124°–126° C.

IR (Nujol): 3350, 1735, 1690 (shoulder), 1650, 1530, 1070 cm$^{-1}$. NMR (CDCl$_3$): δ0.8–1.0 (3H, m), 1.0–2.4 (33H, m), 1.46 (27H, s), 3.0–3.3 (2H, m), 3.6–4.6 (6H, m), 5.15 (12H, s), 7.30 (5H, s).

(2) Step 2

Compound (3) ⟶

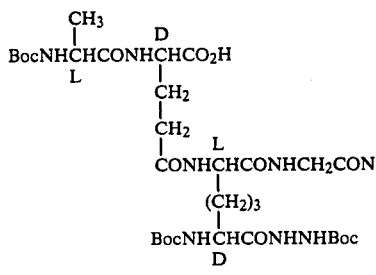

(4)

A solution of Boc-L-Ala-γ-D-Glu(α-OBzl)-(L)-Boc-(D)-mesoDAP-(L)-GlyNHlauryl-(D)-NHNHBoc (3) (0.80 g) in 80% aqueous methanol (25 ml) was hydrogenolyzed in the presence of 10% palladium charcoal (0.1 g). After the catalyst was removed, the solvent was evaporated in vacuo. The residue was treated with diethylether to yield Boc-L-Ala-γ-D-Glu(α-OH)-(L)-Boc-(D)-mesoDAP-(L)-GlyNHlauryl-(D)-NHNHBoc (4) (0.65 g). mp 113°–115° C.

IR (Nujol): 3350, 1720 (shoulder), 1660, 1530, 1070 cm$^{-1}$. NMR (CDCl$_3$): δ0.8–1.0 (3H, m), 1.0–2.5 (33H, m), 1.43 (27H, s), 3.0–3.3 (2H, m), 3.8–4.6 (6H, m).

(3) Step 3

Compound (4) ⟶

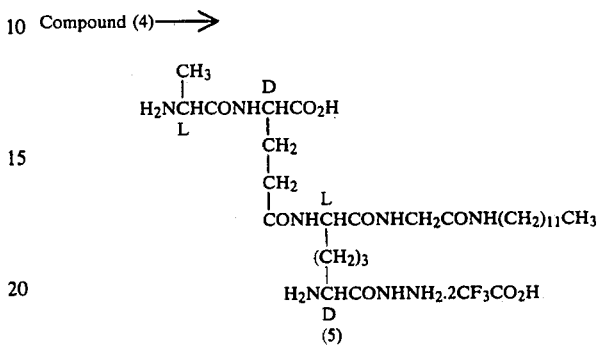

(5)

Boc-L-Ala-γ-D-Glu(α-OH)-(L)-Boc-(D)-mesoDAP-(L)-GlyNHlauryl-(D)-NHNHBoc (4) (0.61 g) was dissolved in trifluoroacetic acid (10 ml) and stirred for 30 minutes at room temperature. The solvent was removed in vacuo. The residue was washed with diethyl ether (20 ml) to give L-Ala-γ-D-Glu(α-OH)-(L)-mesoDAP-(L)-GlyNHlauryl-(D)-NHNH$_2$.2CF$_3$CO$_2$H (5) (0.55 ). mp. 153°–155° C.

NMR (D$_2$O): δ0.8–1.0 (3H, m), 1.0–2.6 (30H, m), 1.60 (3H, d, J=7 Hz), 3.0–3.4 (2H, m), 3.8–4.5 (6H, m).

(4) Step 4

Compound (5) ⟶

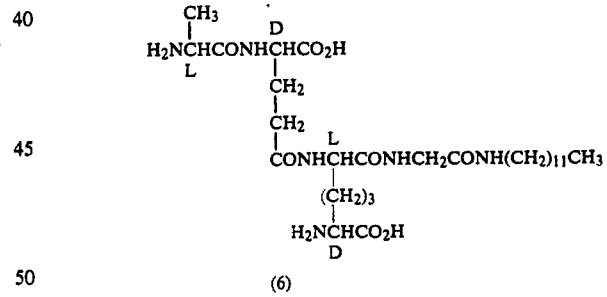

(6)

To a solution of L-Ala-γ-D-Glu(α-OH)-(L)-mesoDAP-(L)-GlyNHlauryl-(D)-NHNH$_2$.2CF$_3$CO$_2$H (5) (0.53 g) in 1N-hydrochloric acid (1 ml) and 1,4-dioxan (4 ml) was added N-bromosuccinimide (0.13 g) at 0° C. with stirring. After stirring for 30 minutes, the mixture was reduced with 2N sodium bisulfite and adjusted at pH 3 with 1M sodium carbonate. After evaporation, the residue was dissolved in water and put on a column of HP-20 (40 ml). After washing with water (200 ml), the column was eluted with 80% aqueous methanol. The eluate was concentrated and lyophilyzed to give L-Ala-γ-D-Glu(α-OH)-(L)-mesoDAP-(L)-GlyNHlauryl (6) (0.17 g). mp. 181°–183° C.

IR (Nujol): 3250, 1640, 1560 cm$^{-1}$. NMR (D$_2$O): δ0.7–1.0 (3H, m), 1.0–2.5 (30H, m), 1.56 (3H, d, J=7 Hz), 3.0–3.3 (2H, m).

EXAMPLE 8

(1) Step 1

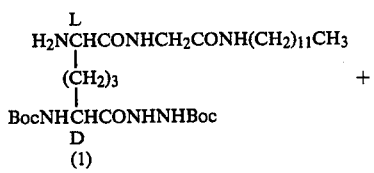

To a solution of Boc-(D)-mesoDAP-(L)-GlyNHlauryl-(D)-NHNHBoc (1) (0.63 g) in dichloromethane (10 ml) was added stearoyl-L-Ala-D-Glu($\alpha$-OBzl)-$\gamma$-Osu (2) (0.68 g) with stirring at 0° C. Stirring was continued overnight at room temperature. After evaporation, the residue was washed with water (10 ml) and ethyl acetate (10 ml), and recrystallized from ethyl acetate to yield stearoyl-L-Ala-$\gamma$-D-Glu($\alpha$-OBzl)-(L)-Boc-(D)-mesoDAP-(L)-GlyNHlauryl-(D)-NHNHBoc (3) (0.83 g). mp. 155°–157° C.

IR (Nujol): 3300, 1730, 1660 (shoulder), 1630, 1530, 1165 cm$^{-1}$. NMR (CDCl$_3$+CO$_3$OD): 0.7–1.0 (6H, m), 1.0–2.0 (79H, m), 2.0–2.5 (4H, m), 2.9–3.5 (2H, m), 3.7–4.0 (2H, m), 5.10 (2H, s), 7.26 (5H, s).

(2) Step 2

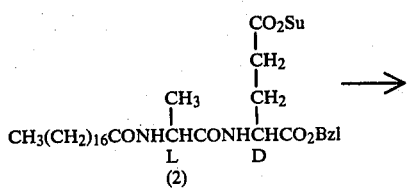

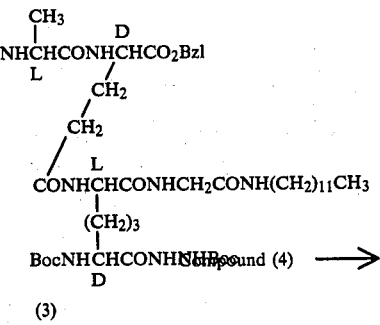

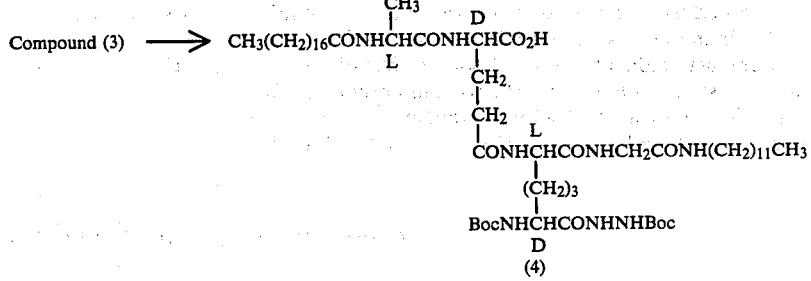

Stearoyl-L-Ala-$\gamma$-D-Glu($\alpha$-OH)-(L)-Boc-(D)-mesoDAP-(L)-GlyNHlauryl-(D)-NHNHBoc (4) was prepared in a similar manner to that of Step 2 of Example 1. mp. 147°–150° C.

IR (Nujol): 3300, 1735, 1630, 1525 cm$^{-1}$. NMR (CDCl$_3$+CD$_3$+OD): $\delta$0.8–1.0 (6H, m), 1.0–2.5 (65H, m), 3.0–3.5 (2H, m), 3.88 (2H, d, J=2 Hz), 4.0–4.5 (4H, m).

(3) Step 3

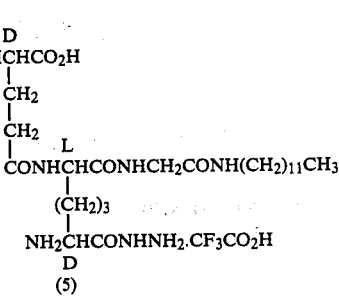

Stearoyl-L-Ala-$\gamma$-D-Glu($\alpha$-OH)-(L)-mesoDAP-(L)-GlyNHlauryl-(D)-NHNH$_2$.CF$_3$CO$_2$H (5) was prepared in a similar manner to that of Step 3 of Example 7. mp. 165°–169° C.

IR (Nujol): 3300, 1710 (shoulder), 1650 (broad) 1540 (broad), 1200, 1140 cm$^{-1}$. NMR (CD$_3$OD): $\delta$0.7–1.1 (3H, m), 1.1–2.5 (67H, m), 3.0–3.5 (2H, m), 3.88 (2H, s), 3.7–4.6 (4H, m).

(4) Step 4

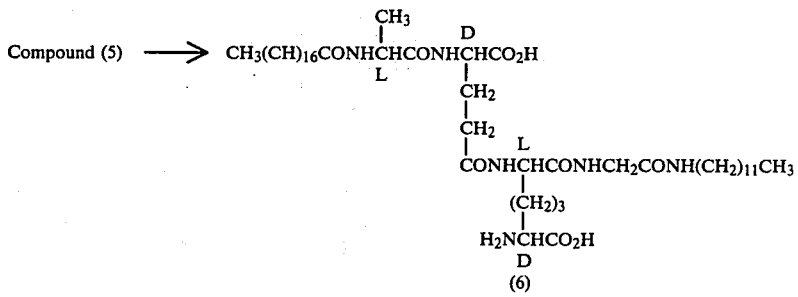

To a solution of stearoyl-L-Ala-γ-D-Glu(α-OH)-(L)-mesoDAP-(L)-GlyNHlauryl-(D)-NHNH$_2$·CF$_3$CO$_2$H (5) in 1N hydrochloric acid (2 ml) and 1,4-dioxane (8 ml) was added N-bromosuccinimide (0.15 g: 0.84 mM) with stirring at 0° C. After stirring for 30 minutes, the mixture was reduced with 3M sodium bisulfite (2 ml) and adjusted at pH 4 with 1M sodium carbonate. The precipitate was washed with ethyl acetate (20 ml) and water (10 ml) and recrystallized from n-butanol to give stearoyl-L-Ala-γ-D-Glu(α-OH)-(L)-mesoDAP-(L)-GlyNHlauryl (6) (0.23 g). mp. 170°–176° C.

IR (Nujol): 3280, 1720 (shoulder), 1620, 1520 cm$^{-1}$. NMR (CF$_3$CO$_2$H): δ0.6–1.0 (6H, m), 1.0–2.9 (65H, m), 3.3–3.6 (2H, m), 4.0–5.0 (6H, m).

EXAMPLE 9

(1) Step 1 prepared in a similar manner to that of step 1 of Example 1.

IR (Nujol): 3300, 1725, 1650 (shoulder), 1640, 1520, 1240, 1165 cm$^{-1}$. NMR (CD$_3$OD): δ0.8–1.0 (3H, m), 1.1–2.0 (52H, m), 2.07 (3H, s), 2.0–2.5 (2H, m), 3.0–3.5 (2H, m), 3.83 (2H, s), 4.0–4.6 (5H, m), 5.17 (2H, s), 7.33 (5H, s).

(2) Step 2

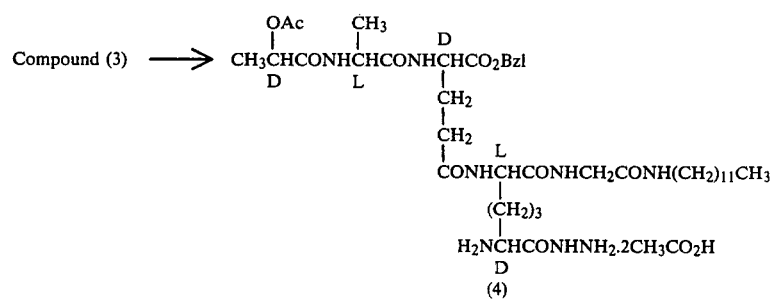

D-Lac(OAc)-L-ALa-γ-D-Glu(α-OBzl)-(L)-mesoDAP-(L)-GlyNHlauryl-(D)-NHNH$_2$·2CF$_3$CO$_2$H (4) was prepared in a similar manner to that of step 3 of Example 7.

NMR (CD$_3$OD): δ0.8–1.0 (3H, m), 1.1–2.0 (34H, m), 2.1 (3H, s), 2.0–2.4 (2H, m), 3.0–3.3 (2H, m), 3.83 (2H, s), 4.0–5.0 (5H, m), 5.17 (2H, s), 7.33 (5H, s).

(3) Step 3

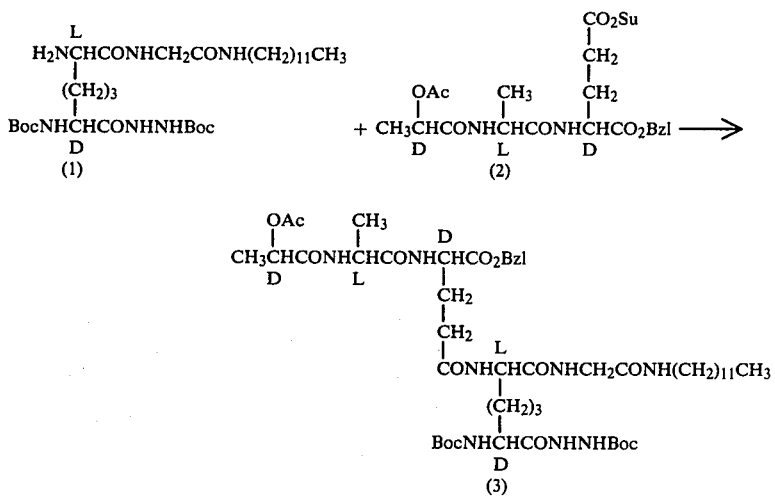

D-Lac(OAc)-L-ALa-γ-D-Glu(α-OBzl)-(L)-Boc-(D)-mesoDAP-(L)-GlyNHlauryl-(D)-NHNHBoc (3) was Compound (4) ⟶
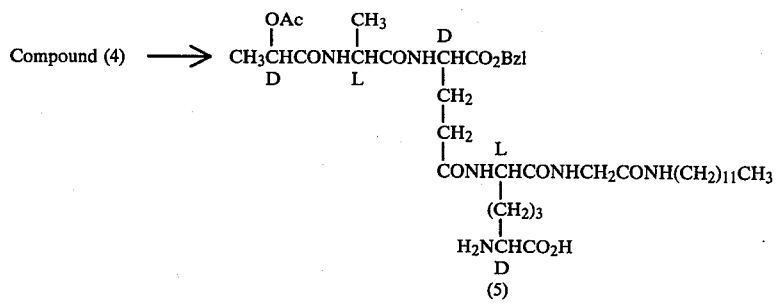

D-Lac(OAc)-L-ALa-γ-D-Glu(α-OBzl)-(L)-mesoDAP-(L)-GlyNHlauryl (5) was prepared in a similar manner to that of step 4 of Example 8. mp. 175°–178° C.

IR (Nujol): 3300, 1730, 1640, 1550, 1250, 1170 cm$^{-1}$.
NMR (CDCl$_3$-CD$_3$OD): δ0.7–1.1 (3H, m), 1.1–2.5 (36H, m), 2.10 (3H, s), 2.9–3.3 (2H, m), 3.5–5.0 (7H, m), 5.15 (2H, s), 7.30 (5H, s).

(4) Step 4

Compound (5) ⟶
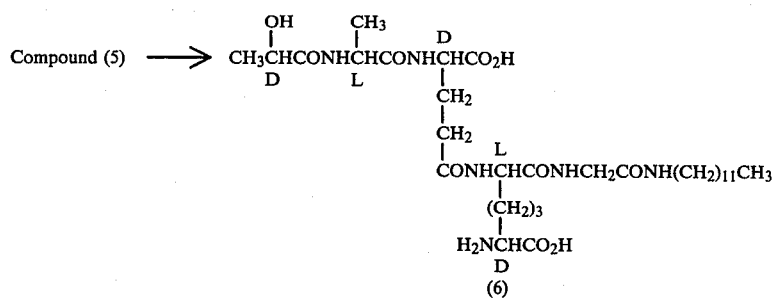

D-Lac-L-ALa-γ-D-Glu(α-OH)-(L)-mesoDAP-(L)-GlyNHlauryl (6) was prepared in a similar manner to that of step 2 of Example 1. mp. 137°–140° C.

IR (Nujol): 3270, 1720 (shoulder), 1620, 1530 cm$^{-1}$.
NMR (D$_2$O): δ0.6–1.0 (3H, m), 1.0–2.4 (36H, m), 3.0–3.4 (2H, m).

EXAMPLE 10

(1) Step 1

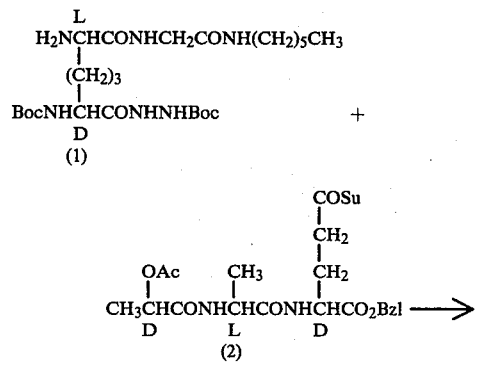

-continued
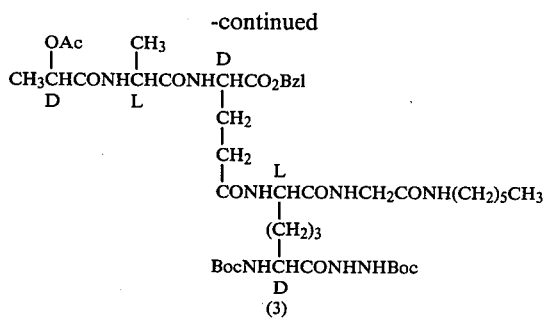

D-Lac(OAc)-L-ALa-γ-D-Glu(α-OBzl)-(L)-Boc-(D)-mesoDAP-(L)-GlyNHhexyl-(D)-NHNHBoc (3) was prepared in a similar manner to that of step 1 of Example 1. mp. 148°–150° C.

IR (Nujol): 3280, 1730, 1650 (shoulder), 1640, 1525, 1240, 1165 cm$^{-1}$. NMR (CD$_3$OD): δ0.8–1.1 (3H, m), 1.1–2.0 (40H, m), 2.10 (3H, s), 2.1–2.5 (2H, m), 3.0–3.5 (2H, m), 3.87 (2H, s), 3.9–5.1 (5H, m), 5.20 (2H, s), 7.37 (5H, s).

(2) Step 2

Compound (3) ⟶
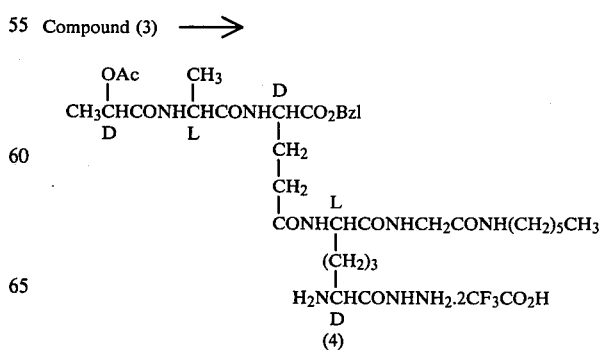

D-Lac(OAc)-L-ALa-γ-D-Glu(α-OBzl)-(L)-mesoDAP-(L)-GlyNHhexyl-(D)-NHNH$_2$.2CF$_3$CO$_2$H (4) was prepared in a similar manner to that of step 3 of Example 7.

IR (Nujol): 3300, 1730, 1660, 1530, 1200 cm$^{-1}$. NMR (CD$_3$OD): δ0.8–1.1 (3H, m), 1.2–2.5 (24H, m), 2.13 (3H, s), 3.0–3.5 (2H, m), 3.90 (2H, s), 4.0–4.6 (5H, m), 5.20 (2H, s), 7.40 (5H, s).

(3) Step 3

Compound (4) ——>

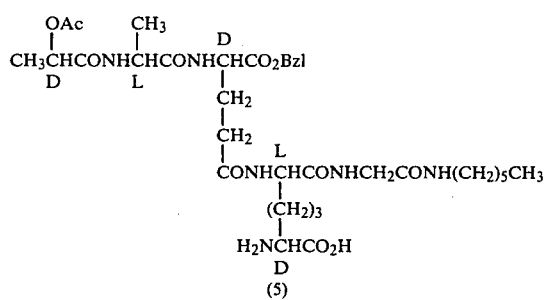

(5)

D-Lac(OAc)-L-ALa-γ-D-Glu(α-OBzl)-(L)-mesoDAP-(L)-GlyNHhexyl (5) was prepared in a similar manner to that of step 4 of Example 8. mp 100°–101° C.

IR (Nujol): 3270, 1735, 1650, 1530, 1230 cm$^{-1}$. NMR (CD$_3$OD): δ0.8–1.1 (3H, m), 1.1–2.0 (28H, m), 2.10 (3H, s), 2.0–2.5 (2H, m), 3.0–3.3 (2H, m), 3.85 (2H, s), 3.9–4.5 (5H, m), 5.16 (2H, s), 7.35 (5H, s).

(4) Step 4

Compound (5) ——>

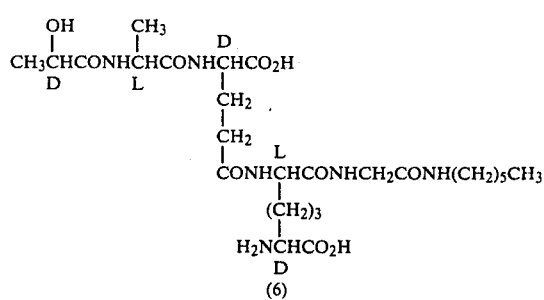

(6)

D-Lac-L-ALa-γ-D-Glu(α-OH)-(L)-mesoDAP-(L)-GlyNHhexyl (6) was prepared in a similar manner to that of Step 2 of Example 1. mp. 135°–138° C.

IR (Nujol): 3500 (shoulder), 3270, 1720 (shoulder), 1640, 1530 cm$^{-1}$. NMR (D$_2$): δ0.7–1.0 (3H, m), 1.36 (3H, d), 1.44 (3H, d), 1.0–2.5 (16H, m), 3.0–3.3 (2H, m), 3.72 (1H, m), 3.86 (2H, s), 4.0–4.5 (4H, m).

EXAMPLE 11

(1) Step 1

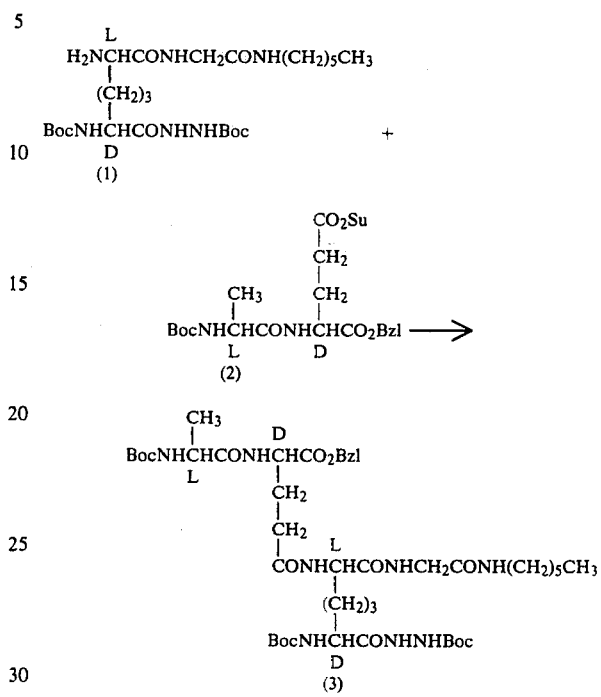

Boc-L-ALa-γ-D-Glu(α-OBzl)-(L)-Boc-(D)-mesoDAP-(L)-GlyNHhexyl-(D)-NHNHBoc (3) was prepared in a similar manner to that of step 1 of Example 1. mp. 110°–112° C.

IR (Nujol): 3350, 1740, 1670 (shoulder), 1650, 1530, 1170 cm$^{-1}$.

NMR (CDCl$_3$): δ0.7–1.1 (3H, m), 1.1–2.0 (46H, m), 2.1–2.7 (2H, m), 3.0–3.5 (2H, m), 3.6–4.6 (6H, m), 5.2 (2H, s), 5.3–5.9 (2H, m), 6.9–7.6 (4H, m), 7.37 (5H, s), 7.7–8.1 (1H, m), 9.0 (1H, m).

(2) Step 2

Compound (3) ——>

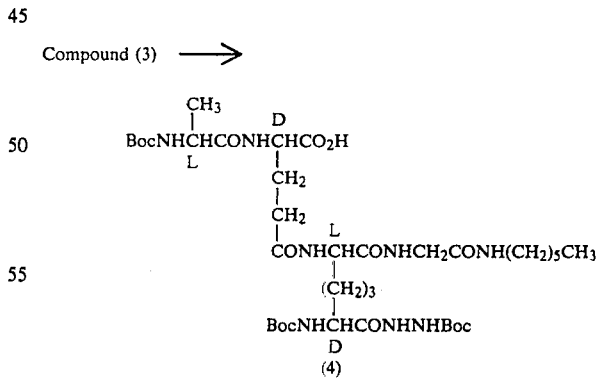

Boc-L-ALa-γ-D-Glu(α-OH)-(L)-Boc-(D)-mesoDAP-(L)-GlyNHhexyl-(D)-NHNHBoc (4) was prepared in a similar manner to that of step 2 of Example 7. mp. 123°–124° C.

IR (Nujol): 3300, 1700 (shoulder), 1660, 1520, 1160 cm$^{-1}$. NMR (CD$_3$OD): δ0.8–1.1 (3H, m), 1.1–2.1 (46H, m), 2.1–2.6 (2H, m), 3.0–3.5 (2H, m), 3.90 (2H, s), 3.9–4.5 (4H, m).

(3) Step 3

Compound (4) ⟶

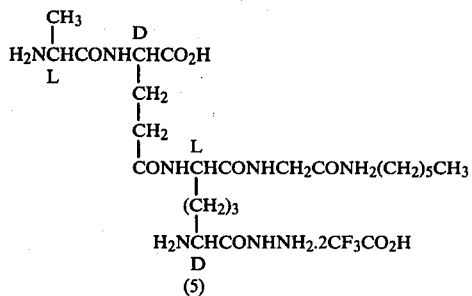
(5)

L-ALa-γ-D-Glu(α-OH)-(L)-mesoDAP-(L)-GlyNH-hexyl-(D)-NHNH$_2$.2CF$_3$CO$_2$H (5) was prepared in a similar manner to that of step 3 of Example 7.

NMR (D$_2$O): δ0.7–1.0 (3H, m), 1.0–2.5 (18H, m), 1.57 (3H, d, J=7 Hz), 3.0–3.3 (2H, m), 3.88 (2H, s), 3.6–4.5 (4H, m).

(4) Step 4

Compound (5) ⟶

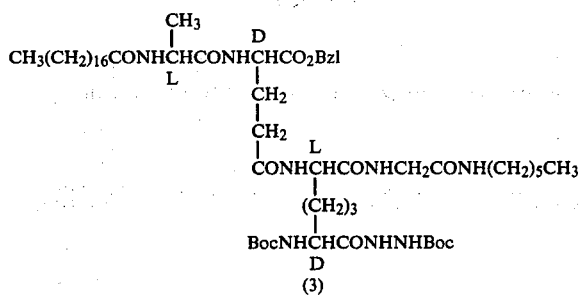
(6)

L-ALa-γ-Glu(α-OH)-(L)-mesoDAP-(L)-GlyNH-hexyl (6) was prepared in a similar manner to that of step 4 of Example 7. mp. 171°–175° C.

IR (Nujol): 3280, 1640, 1550 cm$^{-1}$. NMR (D$_2$O): δ0.7–1.0 (3H, m), 1.0–2.6 (21H, m), 3.0–3.4 (2H, m), 3.6–3.8 (1H, m), 3.82 (2H, s), 3.9–4.4 (3H, m).

EXAMPLE 12

(1) Step 1

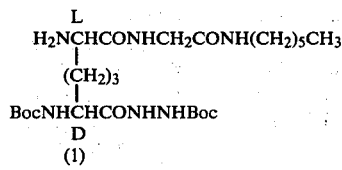 + 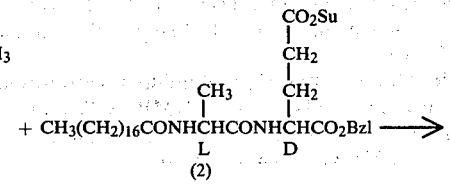 ⟶

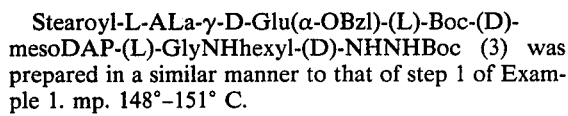
(3)

Stearoyl-L-ALa-γ-D-Glu(α-OBzl)-(L)-Boc-(D)-mesoDAP-(L)-GlyNHhexyl-(D)-NHNHBoc (3) was prepared in a similar manner to that of step 1 of Example 1. mp. 148°–151° C.

IR (Nujol): 3300, 1730, 1660 (shoulder), 1635, 1535, 1170 cm$^{-1}$. NMR (DMSO-d$_6$): δ0.7–1.1 (6H, m), 1.0–2.0 (70H, m), 2.0–2.4 (4H, m), 2.8–3.3 (2H, m), 3.33 (4H, s), 3.5–4.7 (4H, m), 5.13 (2H, s), 7.33 (5H, s).

(2) Step 2

Compound (3) ⟶ 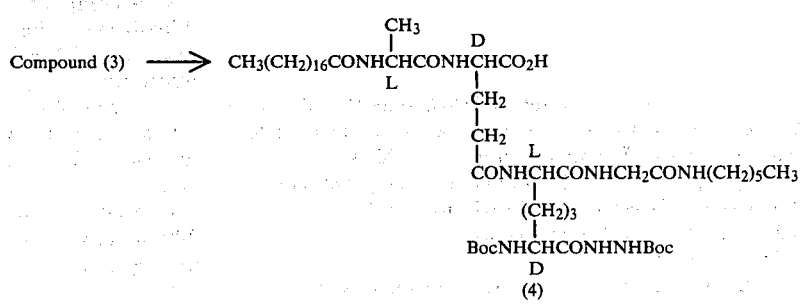
(4)

Stearoyl-L-ALa-γ-D-Glu(α-OH)-(L)-Boc-(D)-mesoDAP-(L)-GlyNHhexyl-(D)-NHNHBoc (4) was prepared in a similar manner to that of step 2 of Example 7. mp. 153°–157° C.

IR (Nujol): 3300, 1730, 1660 (shoulder), 1630, 1530, 1160 cm$^{-1}$. NMR (CD$_3$OD): δ0.8–1.1 (6H, m), 1.1–2.1 (67H, m), 2.0–2.6 (4H, m), 3.1–3.5 (2H, m), 3.90 (2H, s), 4.0–4.6 (4H, m).

(3) Step 3

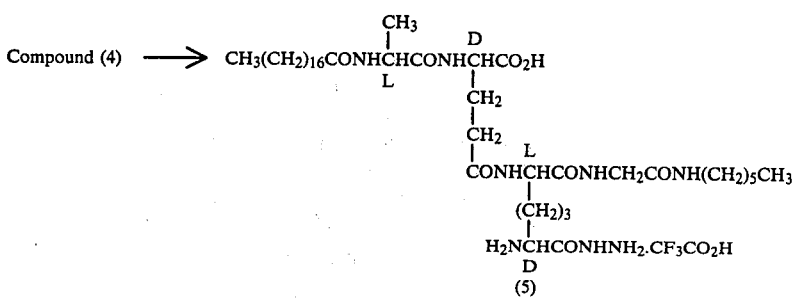

Stearoyl-L-Ala-γ-D-Glu(α-OH)-(L)-mesoDAP-(L)-GlyNHhexyl-(D)-NHNH$_2$.CF$_3$CO$_2$H (5) was prepared in a similar manner to that of step 3 of Example 7. mp. 105°–110° C.

IR (Nujol): 3300, 1705 (shoulder), 1650 (broad), 1540 (broad), 1190, 1140 cm$^{-1}$. NMR (CD$_3$OD): δ0.7–1.1 (3H, m), 1.1–2.1 (49H, m), 2.1–2.5 (4H, m), 3.0–3.5 (2H, m), 3.88 (2H, s), 4.0–4.6 (4H, m).

(4) Step 4

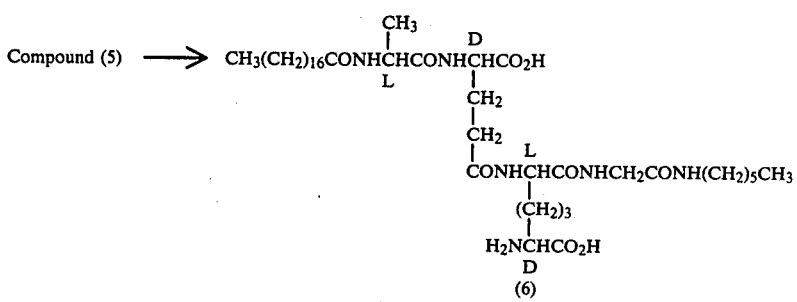

Stearoyl-L-Ala-γ-D-Glu(α-OH)-(L)-mesoDAP-(L)-GlyNHhexyl (6) was prepared in a similar manner to that of step 4 of Example 7. mp. 162°–172° C.

IR (Nujol): 3300, 1720 (shoulder), 1630, 1540 cm$^{-1}$. NMR (CF$_3$CO$_2$H): δ0.6–1.0 (6H, m), 1.0–3.9 (53H, m), 3.2–3.6 (2H, m), 4.0–5.0 (6H, m).

We claim:

1. A compound of the following formula or its pharmaceutically acceptable salt:

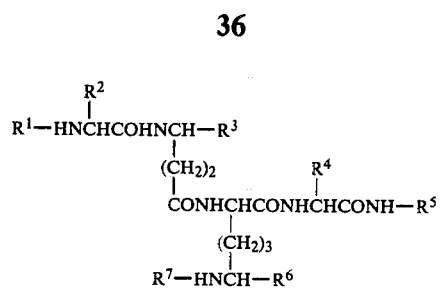

wherein $R^1$ is hydrogen, t-butoxycarbonyl, stearoyl, 2-hydroxypropionyl or 2-acetoxypropionyl, $R^2$ is methyl, $R^3$ is carboxy or benzylcarboxy, $R^4$ is hydrogen, $R^5$ is hydrogen, benzyl, hexyl or lauryl, $R^6$ is carboxy, carbazoyl or t-butoxycarbonylcarbazoyl, and $R^7$ is hydrogen, t-butoxycarbonyl or benzyloxycarbonyl.

2. A compound according to claim 1, wherein $R^1$ is hydrogen, $R^2$ is methyl, $R^3$ is carboxy, $R^4$ is hydrogen, $R^5$ is benzyl, $R^6$ is carboxy, and $R^7$ is hydrogen.

3. A compound according to claim 1, wherein $R^1$ is 2-hydroxypropionyl, $R^2$ is methyl, $R^3$ is carboxy, $R^4$ is hydrogen, $R^5$ is benzyl, $R^6$ is carboxy, and $R^7$ is hydrogen.

4. A compound according to claim 1, wherein $R^1$ is 2-hydroxypropionyl, $R^2$ is methyl, $R^3$ is carboxy, $R^4$ is hydrogen, $R^5$ is hydrogen, $R^6$ is carboxy, and $R^7$ is hydrogen.

5. A compound according to claim 1, wherein $R^1$ is 2-hydroxypropionyl, $R^2$ is methyl, $R^3$ is carboxy, $R^4$ is hydrogen, $R^5$ is lauryl, $R^6$ is carboxy, and $R^7$ is hydrogen.

6. A compound according to claim 1, wherein $R^1$ is 2-hydroxypropionyl, $R^2$ is methyl, $R^3$ is carboxy, $R^4$ is hydrogen, $R^5$ is hexyl, $R^6$ is carboxy, and $R^7$ is hydrogen.

* * * * *